United States Patent [19]
Brown et al.

[11] Patent Number: 5,417,703
[45] Date of Patent: May 23, 1995

[54] THROMBECTOMY DEVICES AND METHODS OF USING SAME

[75] Inventors: Brian Brown, Hanover; Scott Smith, Chaska, both of Minn.

[73] Assignee: SciMed Life Systems, Inc., Maple Grove, Minn.

[21] Appl. No.: 91,338

[22] Filed: Jul. 13, 1993

[51] Int. Cl.⁶ .................... A61B 17/32; A61B 17/22
[52] U.S. Cl. .................... 606/159; 606/171
[58] Field of Search .............. 606/107, 159, 167, 170, 606/171, 180; 604/22

[56] References Cited

U.S. PATENT DOCUMENTS

| | | |
|---|---|---|
| 3,614,953 | 10/1971 | Moss . |
| 3,844,272 | 10/1974 | Banko . |
| 3,937,222 | 2/1976 | Banko . |
| 3,945,375 | 3/1976 | Banko . |
| 4,020,847 | 5/1977 | Clark, III . |
| 4,030,503 | 6/1977 | Clark, III . |
| 4,493,694 | 1/1985 | Wuchinich . |
| 4,516,398 | 5/1985 | Wuchinich . |
| 4,589,412 | 5/1986 | Kensey . |
| 4,598,710 | 7/1986 | Kleinberg et al. .............. 606/170 |
| 4,620,547 | 11/1986 | Boebel .............................. 128/754 |
| 4,631,052 | 12/1986 | Kensey . |
| 4,646,738 | 3/1987 | Trott . |
| 4,664,112 | 5/1987 | Kensey et al. . |
| 4,669,469 | 6/1987 | Gifford, III et al. . |
| 4,676,249 | 6/1987 | Arenas et al. . |
| 4,678,459 | 7/1987 | Onik et al. . |
| 4,679,558 | 7/1987 | Kensey et al. . |
| 4,681,106 | 7/1987 | Kensey et al. . |
| 4,685,458 | 8/1987 | Leckrone ........................... 606/159 |
| 4,696,667 | 9/1987 | Masch ................................ 604/22 |
| 4,700,705 | 10/1987 | Kensey et al. . |
| 4,728,319 | 3/1988 | Masch . |
| 4,729,763 | 3/1988 | Henrie . |
| 4,732,154 | 3/1988 | Shiber . |
| 4,747,821 | 5/1988 | Kensey et al. . |

(List continued on next page.)

FOREIGN PATENT DOCUMENTS 556984  3/1993  Japan ................................ 606/180

OTHER PUBLICATIONS

The American Journal of Cardiology, vol. 60; Aug. 1, 1987; Transcatheter Aspiration of A Thrombus in an Aortocoronary Saphenous Vein Graft; Robert C. Feldman; pp. 379–380.

Aspiration Catheter for Percutaneous Thrombectomy: Clinical Results; Apr. 1990; Rolf W. Guenther et al.; pp. 271–273.

(List continued on next page.)

*Primary Examiner*—Stephen C. Pellegrino
*Assistant Examiner*—Nancy Mulcare
*Attorney, Agent, or Firm*—Nawrocki, Rooney & Sivertson

[57] ABSTRACT

A novel intravascular device for removing vascular occlusion material comprises an elongate tube intravascularly insertable into a patient including a vascular occlusion removal element and a vascular lumen interior surface scouring element. The removal element comprises inner and outer respectively rotatable cutters which may be helical tubular cutters or cutting windows. The cutting windows may include cutting edges defining a substantially rectangular, arcuate or V-shaped configuration. The scouring element may be a flexible wire or a dilating member engageable with an interior surface of a vascular lumen. The scouring element may include a web member for collecting and funneling scoured material. A novel method for removing vascular occlusion material from a vascular lumen having an interior surface is also provided. The method comprises the steps of: providing an intravascular device having vascular occlusion removal means and vascular lumen scouring means; inserting the device intravascularly into a patient; positioning the device adjacent vascular occlusion material within the vascular lumen; energizing the removal means for removing vascular occlusion material from the vascular lumen; and energizing the scouring means for scouring the interior surface of the vascular lumen.

24 Claims, 7 Drawing Sheets

U.S. PATENT DOCUMENTS

| | | |
|---|---|---|
| 4,749,376 | 6/1988 | Kensey et al. . |
| 4,771,774 | 9/1988 | Simpson et al. . |
| 4,784,636 | 11/1988 | Rydell . |
| 4,819,634 | 4/1989 | Shiber . |
| 4,819,635 | 4/1989 | Shapiro ............... 604/22 |
| 4,846,192 | 7/1989 | Stuart ................. 128/752 |
| 4,850,354 | 7/1989 | McGurk-Burleson et al. .... 606/180 |
| 4,857,045 | 8/1989 | Rydell . |
| 4,857,046 | 8/1989 | Stevens et al. . |
| 4,886,061 | 12/1989 | Fischell et al. . |
| 4,913,698 | 4/1990 | Ito et al. . |
| 4,917,085 | 4/1990 | Smith . |
| 4,926,858 | 5/1990 | Gifford, III et al. . |
| 4,957,482 | 9/1990 | Shiber . |
| 4,979,939 | 12/1990 | Shiber . |
| 4,979,951 | 12/1990 | Simpson ............... 606/159 |
| 4,994,067 | 2/1991 | Summers ............... 606/159 |
| 4,998,919 | 3/1991 | Schnepp-Pesch et al. . |
| 5,007,896 | 4/1991 | Shiber . |
| 5,011,488 | 4/1991 | Ginsburg . |
| 5,030,201 | 7/1991 | Palestrant ............... 604/22 |
| 5,042,984 | 8/1991 | Kensey et al. . |
| 5,052,404 | 10/1991 | Hodgson . |
| 5,059,178 | 10/1991 | Ya . |
| 5,071,425 | 12/1991 | Gifford, III et al. . |
| 5,074,841 | 12/1991 | Ademovic et al. ............ 604/22 |
| 5,085,662 | 2/1992 | Willard . |
| 5,087,265 | 2/1992 | Summers ............... 606/159 |
| 5,092,839 | 3/1992 | Kipperman . |
| 5,092,873 | 3/1992 | Simpson et al. . |
| 5,100,424 | 3/1992 | Jang et al. . |
| 5,114,399 | 5/1992 | Kovalcheck . |
| 5,158,564 | 10/1992 | Schnepp-Pesch et al. ......... 606/159 |
| 5,192,291 | 3/1993 | Pannek, Jr. .................. 606/159 |
| 5,224,488 | 7/1993 | Neuffer ................. 606/170 |
| 5,242,460 | 9/1993 | Klein et al. ............ 606/159 |
| 5,282,484 | 2/1994 | Reger ................ 606/159 |

OTHER PUBLICATIONS

Journal of Thoracic & Cardiovasc Surg. (1962) 44; Endovascular Suction Catheters; For Thrombectomy and Embolectomy; W. Andrew Dale; pp. 557–558.

Angiology 12 (1961); The Roto–Drill, A New Instrument For Thromboendarterectomy; B. G. P. Shafiroff, M.D.; pp. 316–319.

Stereotact Funct. Neurosurg 1989:53:77–84; Stereotactic Aqua Stream and Aspirator for Hypertensive Intracerebral Hematoma; Haruhide Ito et al; pp. 77–84.

Neurosurgery; vol. 25, No. 3, 1989; Mechanical Aspiration of Hematomas in an in Vitro Mode; Howard H. Kaufman et al.; pp. 347–350.

Arch Ophthal; vol. 86, Nov. 1971; Experimental Vitrectomy; Instrumentation and Surgical Technique; Gholam A. Peyman et al.; pp. 548–551.

Surgical Dynamics; Nucleotome System; Automated Percutaneous Lumbar Discectomy; Diagnosis: Treatment of Choice: Automated Percutaneous Lumbar Discectomy; 1990.

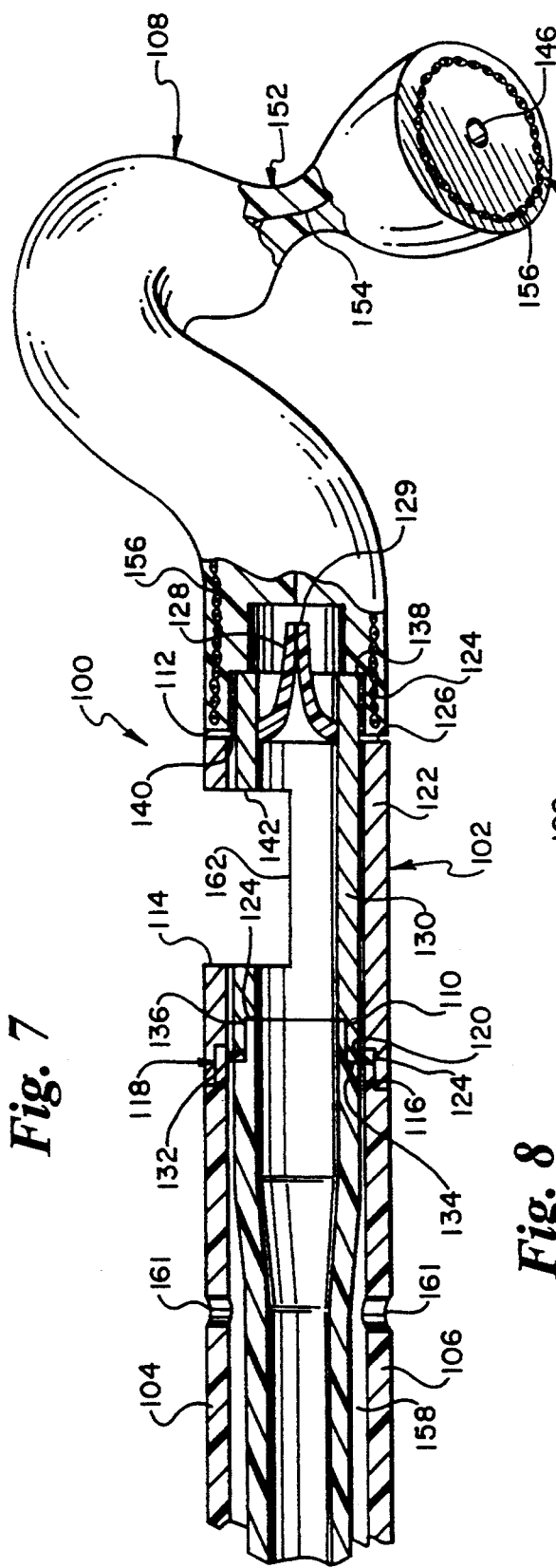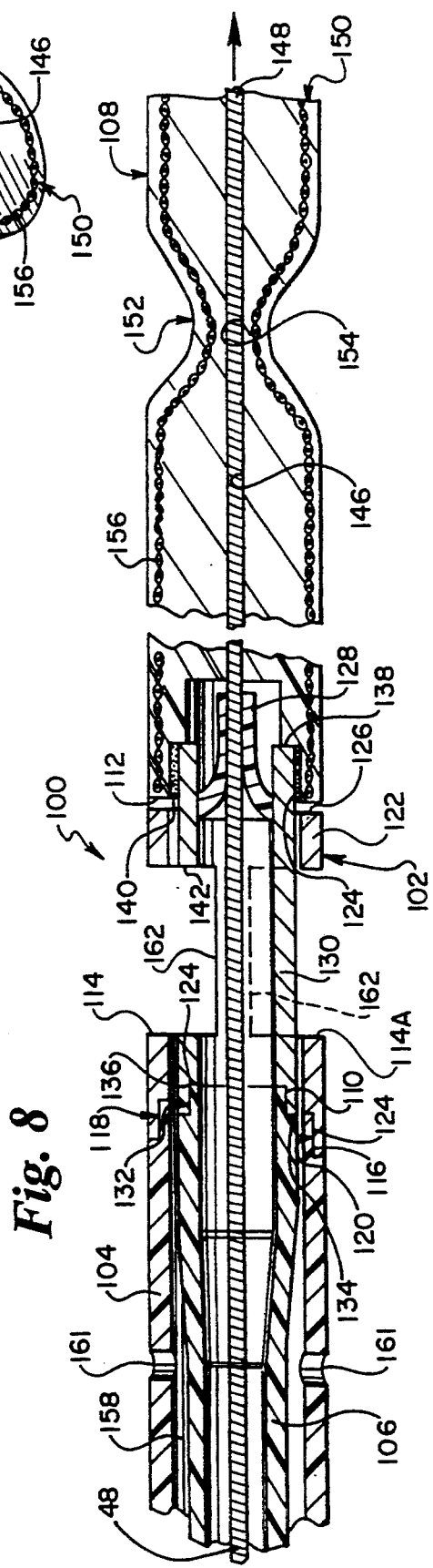

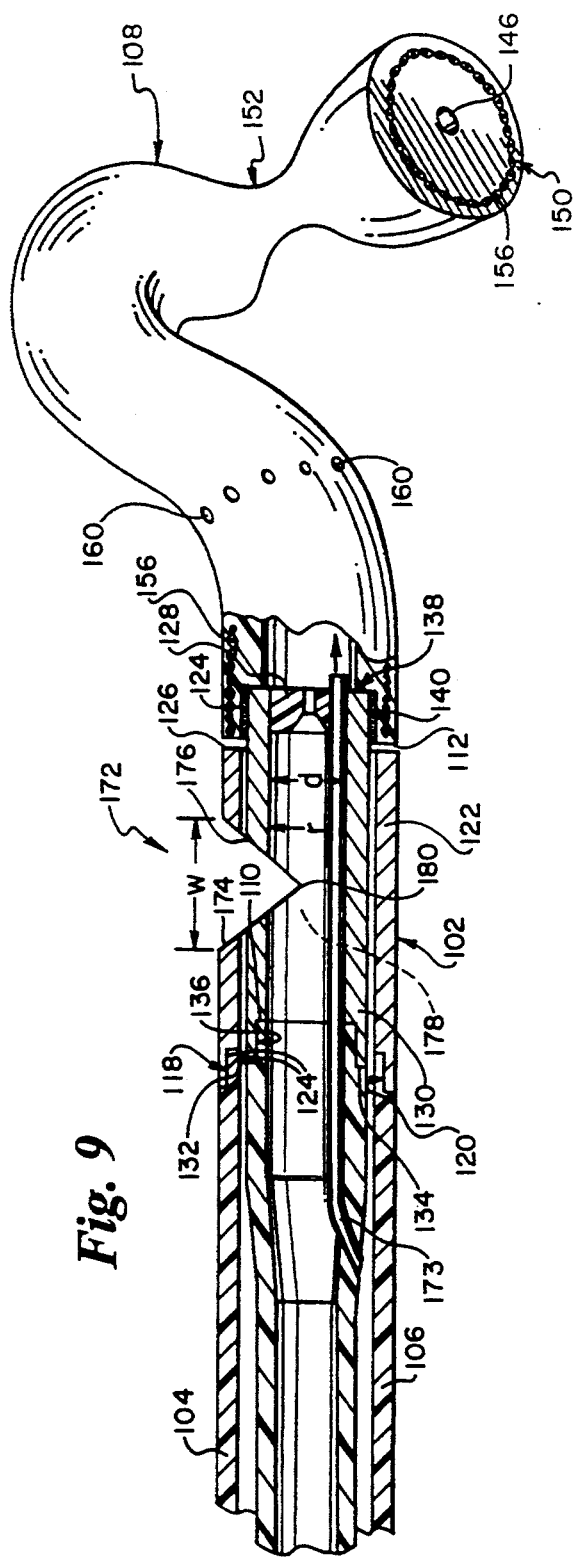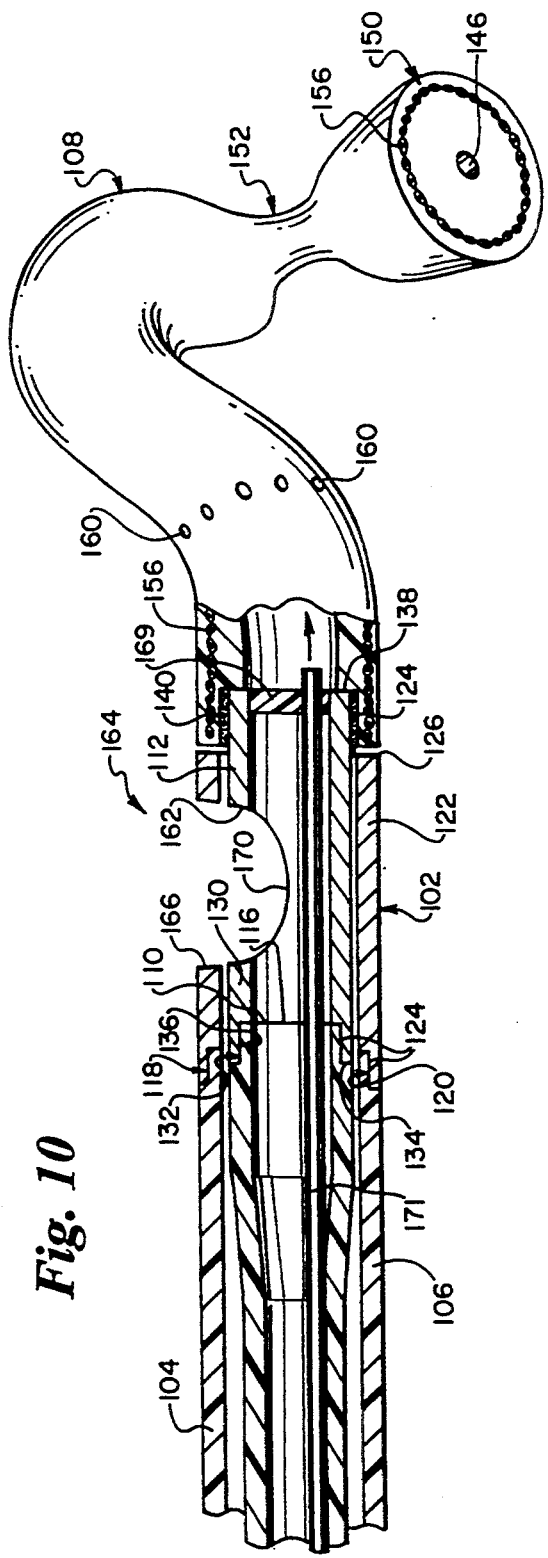

1

THROMBECTOMY DEVICES AND METHODS OF USING SAME

BACKGROUND OF THE INVENTION

The present invention relates generally to novel devices for removing intravascular deposits, occlusions, and the like from a vascular system. More specifically, the invention relates to novel intravascular thrombectomy devices and methods of using the same.

Vascular diseases, such as arteriosclerosis and the like, inflict an ever increasing number of people in modern times. Some of these diseases are caused by deposits or growths formed within a vascular lumen, which may be located in the coronary, peripheral, or other vasculature. These deposits can be formed in a plurality of ways, may be formed from hard, calcified tissues or materials, thereby forming an atheroma, and the like, or may be formed from material free floating within the vascular system, like an embolus, which may become attached or lodged in a certain portion of the vasculature. Other deposits may be formed from soft tissues, such as a blood clot, growing in a relatively fixed place in the vasculature, such as a thrombus.

These various deposits or occlusions may only constrict a vascular lumen, thereby reducing blood flow through a particular portion of the vasculature, or may form a total occlusion of a particular lumen, thereby severely limiting or cutting off blood circulation to particular parts of a patient's body. Total occlusions can be of heightened concern if the occluded lumen supplies blood to a vital organ. In any case, such occlusions, whether partial or complete, can compromise a patient's health and well-being.

In an effort to alleviate some of the problems caused by the occlusions, many various methods of treatment have been developed in an effort to restore substantially normal circulation through the diseased portion of the vasculature. While invasive procedures, such as vascular bypasses, may be effective, it is desirable to use non-invasive, intravascular methods of treatment. By using these non-invasive procedures, the patient can experience less post-operative pain, necessary rehabilitation and a lower probability of infection.

One such non-invasive method is conventional balloon angioplasty wherein a balloon catheter is inserted intravascularly into a patient. The balloon catheter includes a dilating member which is placed adjacent the vascular occlusion and then is inflated. Intravascular inflation of the dilating member by sufficient pressures, on the order of 5 atmospheres, causes it to compress or mold the occluding matter to revascularize the occluded lumen thereby restoring substantially normal blood flow through the revascularized portion. It is to be noted, however, that this procedure only molds the occluding matter and does not remove that matter from the patient's vasculature.

While treatment by conventional balloon angioplasty can be quite successful in substantially removing some vascular occlusions, other occlusions may be difficult to remove by angioplasty, thereby making conventional angioplasty, by itself, an insufficient treatment method in some instances. Specifically, some intravascular occlusions may be composed of a particularly hard, rigid material which is not prone or susceptible to angioplastic molding. Such rigid occlusions may require pressures to mold the occlusion greater than those reasonably safe to introduce into a patient's vasculature. This consideration may take on added significance if the particular portion of the patient's vasculature to be treated is structurally weak.

Furthermore, if the occlusion is a blood clot or soft tissue thrombus, such as those that may occur in the peripheral vasculature, for instance, the soft tissues of the thrombus may sufficiently resist the molding action of the dilating member (i.e. may be too elastic) to prevent conventional angioplasty from permanently restoring vascular blood flow. In addition, even if the occlusion is successfully molded, thereby revascularizing the vessel and restoring blood flow therethrough, there is a chance that the occlusion may recur because the occluding material is not removed from the vascular lumen, thereby necessitating repeated or alternative treatments.

Given these considerations regarding conventional balloon angioplasty, other alternative methods of non-invasive, intravascular treatment have been developed in an effort to provide another way of revascularizing an occluded vessel and of restoring blood flow through the relevant vasculature. These adjunct treatments may offer a more effective alternative treatment to some patients than conventional balloon angioplasty, may have particular utility with a particular vascular occlusion., or may provide added benefits to a patient when combined with traditional balloon angioplasty.

Accordingly, the present invention is intended to provide novel treatment means or methods for .removing such a soft tissue vascular occlusion material, such as a thrombus and the like, from a patient's vasculature. It is desirable for the invention to provide an intravascular treatment device for removing soft tissue obstructions from a vascular lumen, such as that located within the peripheral vasculature, for example. Ideally, the invention also provides novel methods for removing vascular occlusions, especially soft tissue occlusions.

SUMMARY OF THE INVENTION

A general object of the present invention is to provide a novel intravascular treatment device.

A more specific object of the invention is to provide a novel intravascular treatment device which is particularly adept at removing soft tissue occlusions, such as thrombus and the like, from an interior surface of a vascular lumen.

Another object of the present invention is to provide a novel thrombectomy device which can scour an interior surface of a patient's vasculature.

An additional object of the invention is to provide a novel thrombectomy device having scouring means positioned relative to a cutting window such that occlusion material scoured from a vascular lumen interior surface by the scouring means will move into the cutting window.

A further object of the present invention is to provide a novel thrombectomy device which can irrigate an intravascular treatment site.

Another object of the invention is to provide a novel thrombectomy device which operates at a relatively low rotational speed, on the order of 100 to 1,000 revolutions per minute.

An additional object of the present invention is to provide a novel thrombectomy device which resists "pull back" of a helical cutter during operation thereof.

Another object of the present invention is to provide a novel thrombectomy device which can control torsional deformation thereof.

A further object of the present invention is to provide novel methods for removing vascular occlusion material from an interior surface of a vascular lumen.

A novel intravascular device, constructed according to the teachings of the present invention, for removing vascular occlusion material comprises an elongate tube intravascularly insertable into a patient including a vascular occlusion removal element and a vascular lumen interior surface scouring element. The removal element comprises inner and outer respectively rotatable cutters which may be helical tubular cutters or cutting windows. The cutting windows may include cutting edges extending substantially parallel to the axis of the device defining a substantially rectangular, arcuate or V-shaped configuration. The scouring element may be a flexible wire or a dilating member engageable with an interior surface of a vascular lumen. The scouring element may include a web member for collecting and funneling scoured material.

A novel method for removing vascular occlusion material from a vascular lumen having an interior surface is also provided. The method comprises the steps of: providing an intravascular device having vascular occlusion removal means and vascular lumen scouring means; inserting the device intravascularly into a patient; positioning the device adjacent vascular occlusion material within the vascular lumen; energizing the removal means for removing vascular occlusion material from the vascular lumen; and energizing the scouring means for scouring the interior surface of the vascular lumen.

BRIEF DESCRIPTION OF THE DRAWINGS

The organization and manner of the structure and operation of the invention, together with further objects and advantages thereof, may best be understood by reference to the following description taken in connection with the accompanying drawings, wherein like reference numerals identify like elements in which:

FIG. 7 is a sectioned side elevational view of another embodiment of the invention having a non-linear pigtail member for scouring an interior surface of a vascular lumen;

FIG. 8 is a view, similar to that of FIG. 7, of an additional novel thrombectomy device having multiple cutting windows, and showing a pigtail member substantially straightened by the insertion of a guidewire therein;

FIG. 9 is an enlarged view, similar to that of FIG. 7, of a further embodiment of the invention having a substantially angularly configured cutting window;

FIG. 10 is a view, similar to that of FIG. 7, of another thrombectomy device of the invention including a substantially arcuate cutting window;

DETAILED DESCRIPTION OF PREFERRED EMBODIMENTS

Figure 1:
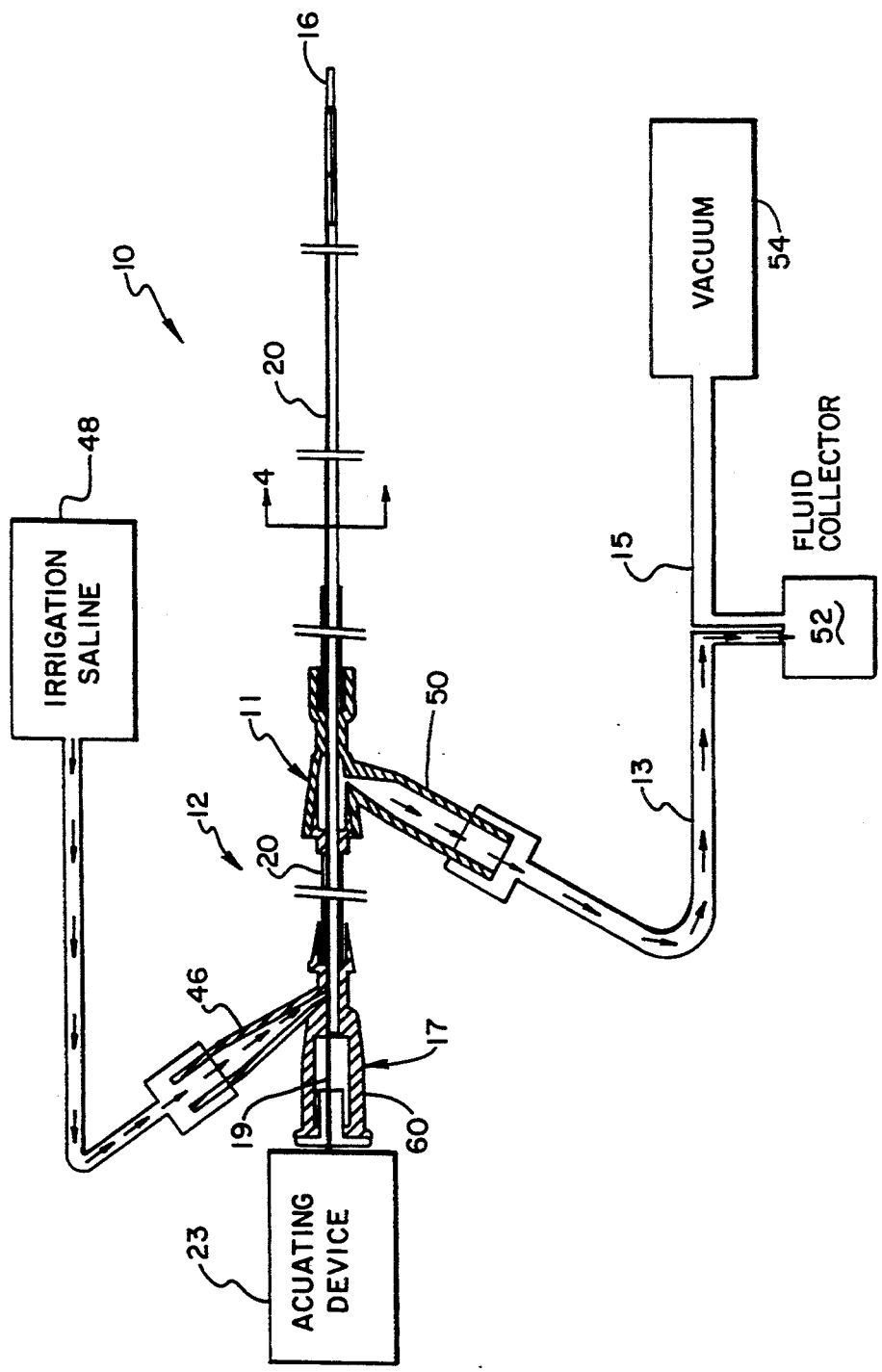
FIG. 1 is a cross-sectional side view of the preferred embodiment of the thrombus extraction device including the manifold system located at the proximal end.

While the invention may be susceptible to embodiment in different forms, there are shown in the drawings, and herein will be described in detail, specific embodiments with the understanding that the present disclosure is to be considered an exemplification of the principles of the invention, and is not intended to limit the invention to that as illustrated and described herein.

Figure 3:
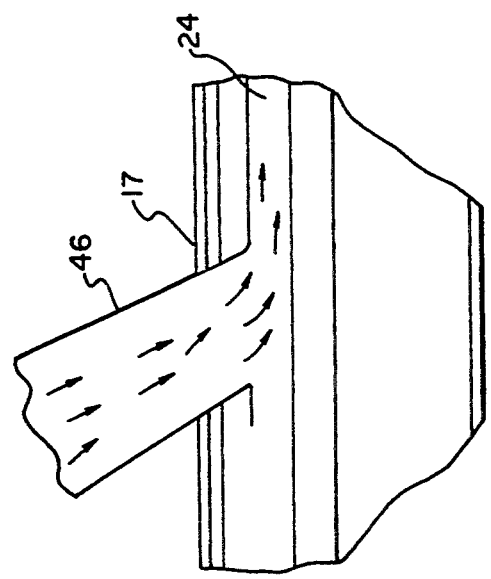
FIG. 3 is an enlarged cross-sectional view of a section of the proximal manifold including arrows that represent the flow of fluid through the first lumen.
Figure 2:
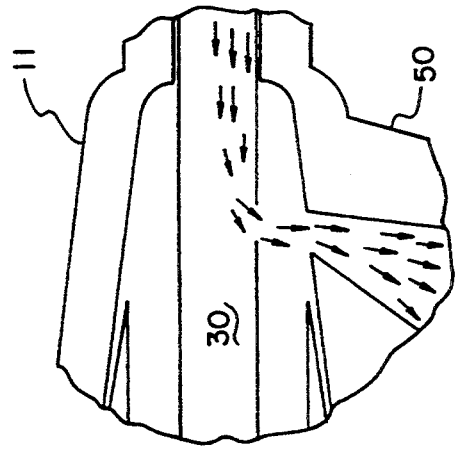
FIG. 2 is an enlarged cross-sectional view of a section of the distal manifold including arrows that represent the flow of fluid from the distal end of the thrombus extraction device into the fluid collector.

FIGS. 1 through 3 show the basic construction of the preferred embodiment of the device. FIG. 1 is an overall cross-sectional side view of the entire thrombectomy device 10 including the manifold system 12 which is located at the proximal end.

The manifold system 12 includes a distal manifold 11 having a port 50 through which a vacuum or negative pressure is applied to lumen 30. The port 50 is connected through a conduit 13 to a fluid collector 52 which is connected through a conduit 15 to a vacuum pump 54. The vacuum pump 54 can be regulated and adjusted to control the negative pressure. FIG. 2 is an enlarged cross section view taken through the distal manifold 11.

A proximal manifold 17 is connected to distal manifold 11 by a hollow outer tube 20 which extends to the distal end of the device 10. Irrigation fluid such as saline is stored in a fluid supply means 48 from which it is pumped through port 46 of the proximal manifold 17. Fluid under pressure flows from port 46 into a lumen 24 that extends through outer tube 20. FIG. 3 is an enlarged cross section view of the proximal manifold 17.

A cutter actuating device 23 is connected to the proximal end of the manifold system 12 which functions to rotate the cutter tubes in the appropriate direction or directions.

It is to be noted that, the invention will be discussed with respect to particular embodiments and their employment in removing soft tissue occlusions, however, it is to be noted that the teachings, embodiments, and methods of the present invention can be utilized for the removal of occlusion material of other composition without departing from the intended scope of the invention. The scope of the invention is not to be limited by the construction of the associated prime mover.

Figure 4:
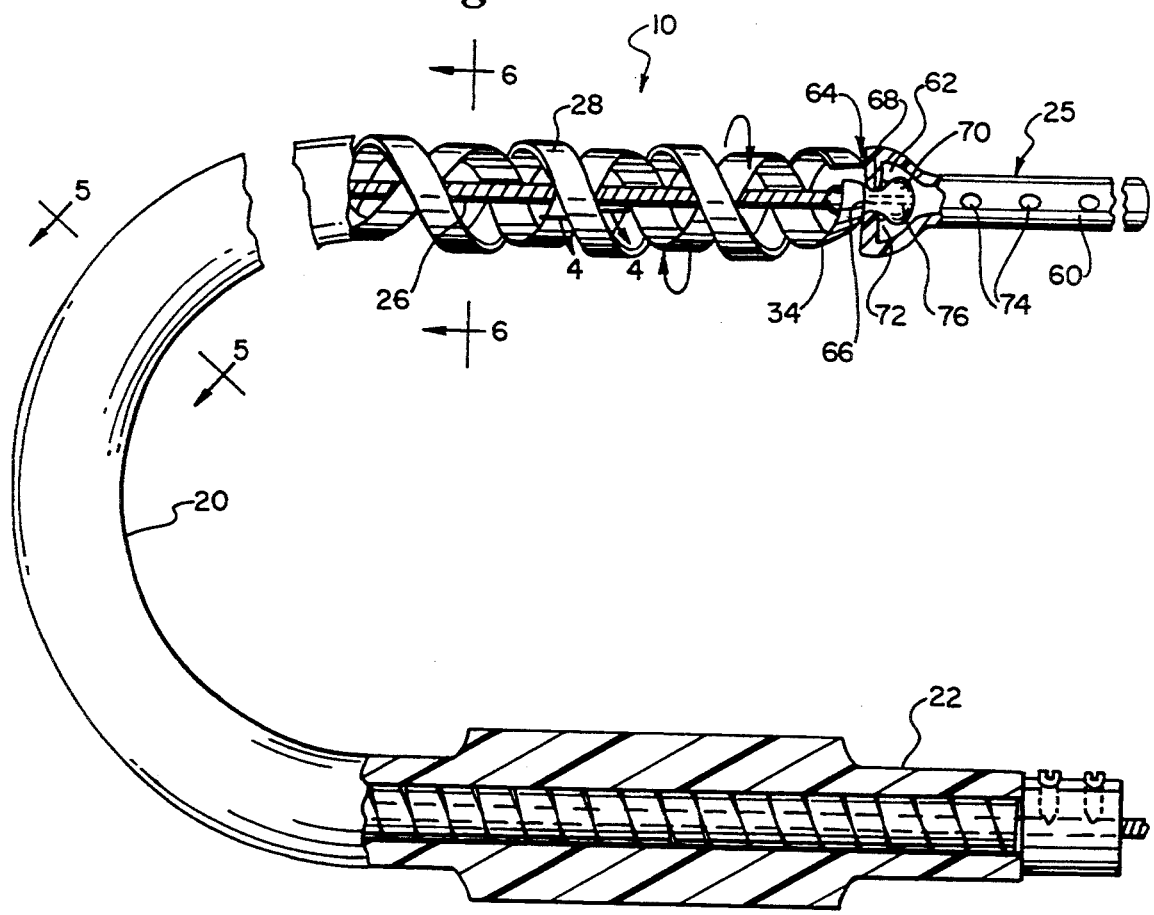
FIG. 4 is a fractured, partially sectioned side elevational view of a novel thrombectomy device, constructed according to the teachings of the present invention, comprising a rotatable helical cutter for removing deposits, such as thrombus, from vasculature.
Figure 5:
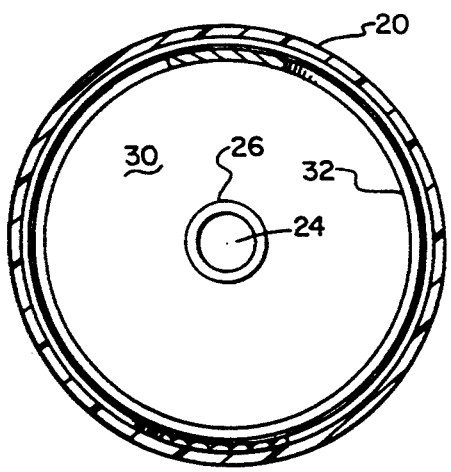
FIG. 5 is a sectional view, taken along line 5—5 of FIG. 4, showing the particular relative orientation of helixes of the embodiment of FIG. 4.
Figure 6:
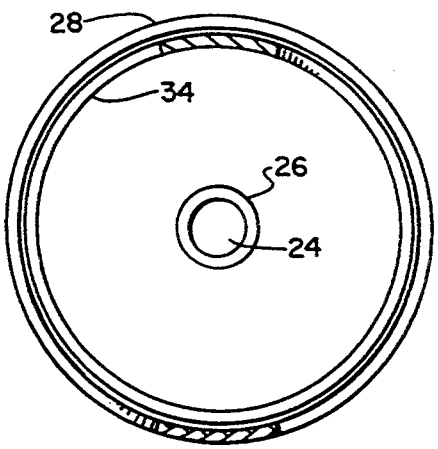
FIG. 6 is a sectional view, taken along line 6—6 of FIG. 4, showing the novel luminal construction of the device.

An embodiment of the invention is illustrated in FIGS. 4 through 6. The thrombectomy device 1.0 of this embodiment includes a hollow outer tube 20 that extends from the proximal end 22 to the distal end 25. The distal end portion of outer tube 20 consist of a helical cutter element 28.

An inner tube 32 having an outer diameter that is less than the inner diameter of outer tube 20 is positioned within outer tube 20. A lumen 30 extends through the center of inner tube 32. There is sufficient clearance between the outer surface of inner tube 32 and the inner surface of outer tube 20 to permit relative rotation between tubes 26 and 32. The distal end portion of inner tube 32 consist of a helical cutter element 34.

The helical cutting elements 28 and 34 are comprised of a suitable material, such as stainless steel, either wound from a ribbon or cut from a hypotube, and are attached to the inner and outer tubes to enable relative rotation one to the other.

An inner shaft 26 has a lumen 24 of a size to permit the passage of a guide wire and/or irrigation fluid. The distal end of helical cutter element 34 is connected to the distal end of inner shaft 26 such that rotary movement of inner shaft 26 can be transmitted to helical cutter element 34. The proximal end of inner shaft 26 exits the proximal manifold 17 and is drivingly connected to the cutter actuating mechanism 23.

A distal tip member 60 having an inner cavity 62 is secured at 64 to the distal end of helical cutter element 28. An extension 66, of inner shaft 26 extends through an opening 68 formed in distal tip member 60, terminates in a bulb member 70. A seal 72 is provided between extension 66 and opening 68 to prevent fluid flow therebetween. A lumen 76 extends through distal tip member 60 through which fluid can flow from lumen 24 into the cavity 62. A plurality of openings 74 are formed in distal tip member 60 through which fluid from cavity 62 can excape into the patient's vessel.

As the inner 32 and outer 20 tubes rotate relative to one another, negative pressure is applied to the lumen 30 of the inner tube 32, and irrigation fluid may be supplied through lumen 24 of inner shaft 26, so that a thrombus-fluid mixture is aspirated through the inner rotating tube 32.

Another embodiment of the invention is an occlusion material removal or thrombectomy device 100, a distal end 102 of which is illustrated in FIG. 7. The proximal end of the thrombectomy device 100 can be of any suitable construction, may be substantially similar to the proximal end construction illustrated in FIG. 4, and is appropriately attached to a prime mover, as discussed hereinabove, which is capable of inducing rotations substantially within the range of 100 to 100,000 revolutions per minute. The distal end 102 of the thrombectomy device 100 comprises an outer tube 104, preferably of a braided or otherwise reinforced construction, a rotatable inner tube 106, preferably comprising a torque shaft, and a flexible member or pigtail member 108 fixedly attached adjacent a distal end 110 of the inner tube 106 such that the inner tube 106 and the pigtail member 108 rotate conjointly under the influence of the prime mover. The precise construction of this fixed attachment will be discussed shortly. Similar to the operation of the device 10, rotation of the inner tube 106 relative to the outer tube 104 allows the thrombectomy device 100 to remove vascular occlusion material from a vascular lumen.

The outer tube 104 has an axial length sufficient to extend from a distal end of a prime mover, not shown, towards a proximal end 112 of the pigtail member 108, has an inner diameter sufficient to accept the inner tube 106 such that the inner tube 106 is coaxially disposed within the outer tube 104, and has an outer diameter small enough to be inserted into a vascular lumen to be revascularized. The outer surface of the outer tube 104 may be coated with a lubricious substance, such as TEFLON® and the like, for facilitating intravascular navigation of the device 100. The outer diameter of the outer tube 104 is substantially equal to the outer diameter of the proximal end 112 of the pigtail member 108 such that the distal end 102 of the thrombectomy device 100 presents a substantially smooth outer surface profile for facilitating intravascular insertion and navigation of the thrombectomy device 100.

The outer tube 104 includes an opening or cutting window 114 having a substantially rectangular configuration, located adjacent a distal end 116 thereof for accepting vascular occlusion material to be removed. Specifically, the distal end 116 of the outer tube 104 has a reduced outer diameter portion 118 which mates with a complementary increased inner diameter portion 120 of a cylindrical member 122, preferably formed from stainless steel, including the cutting window 114, for forming a lap joint between the distal end of the outer tube 104 and the proximal end of the cylindrical member 122. A bead of a suitable adhesive means 124, such as an epoxy, a urethane or a cyanoacrylate, for example, can be provided between the reduced outer diameter portion 118 of the outer tube 104 and the increased inner diameter portion 120 of the cylindrical member 122 to insure a firm bond between the outer tube 104 and the cylindrical member 122. In some constructions of the thrombectomy device 100, the outer tube 104 itself can include the cutting window 114, thereby eliminating the need for the cylindrical member 122. In another embodiment of the invention as shown in FIG. 8, a second cutting window 114A, substantially similar to the cutting window 114 but offset substantially diametrically therefrom, may be provided on the cylindrical member 122 for changing the cutting characteristics of the thrombectomy device 100.

It is to be noted that the cutting window 114 exists only on a subset of an outer diameter surface of the cylindrical member 122, and that the particular configuration of the cutting window 114 may be altered as desired, as will become more clear hereinafter. A distal end 126 of the cylindrical member 122 abuts the proximal end 112 of the pigtail member 108, but there is sufficient clearance between the proximal end 112 and the distal end 126 so that the pigtail member 108 can rotate independently of the outer tube 104 and the cylindrical member 122 for removing vascular occlusion material or scouring a vascular lumen, as will be discussed in greater detail later.

The inner tube 106 has an outer diameter smaller than the inner diameter of the outer tube 104 to facilitate relative rotation of the tubes 104 and 106. The inner tube 106 has an axial length sufficient to extend from a distal end of a drive shaft, not shown, towards the proximal end 112 of the pigtail member 108. A distal end 128 of the inner tube 106 is operatively connected to the proximal end 112 of the pigtail member 108 so that forces applied to the inner tube 106 by the drive shaft can be transmitted to the pigtail member 108. Thus, the pigtail member 108 can be energized for scouring an inner diameter surface of a vascular lumen to be treated. It is envisioned that, in some constructions, the inner tube 106 may be provided as the drive shaft, thereby being directly coupled to the prime mover. The inner tube 106 has an inner diameter of suitable length to allow the inner tube 106 to accept vascular occlusion material removed from a thrombus and the like, thereby allowing a negative pressure to be applied to the interior of the inner tube 106 to aspirate the intravascular treatment site and allow occlusion material severed by the cutting window 114 to be completely removed from a patient's vasculature.

To facilitate vascular occlusion material removal, the distal end 110 of the inner tube 106 is fixedly attached to a cylindrical member 130, constructed substantially similarly to the cylindrical member 122. Specifically, the distal end 110 of the inner tube 106 includes a reduced outer diameter section 132 and a proximal end 134 of the cylindrical member 130 has a complementary increased inner diameter segment 136 which are interengageable to form a lap joint between the inner tube 106 and the cylindrical member 130. A bead of adhesive means 124 can also be provided to insure a firm bond between the inner tube 106 and the cylindrical member 130, thereby facilitating conjoint rotation of the cylindrical member 130 and the inner tube 106.

The cylindrical member 130 has an outer diameter substantially equal to the outer diameter of the inner tube 106 and smaller than the inner diameter of the cylindrical member 122 such that the cylindrical member 130 can rotate freely within the cylindrical member 122. A distal end 138 of the cylindrical member 130 extends distally beyond the distal end 126 of the cylindrical member 122. This extension forms a pigtail mounting surface 140 to which the proximal end 112 of the pigtail member 108 is fixedly attached by means of adhesive 124 such that the pigtail member 108 rotates conjointly with the cylindrical member 130 and the inner tube 106. The extension of the distal end 138 into the pigtail member 108 provides for a smooth transition of flexibility from the inner tube 106 and the outer tube 104, and the cylindrical members 122 and 130, to the pigtail member 108.

The cylindrical member 130 has a cutting window 142 thereon constructed substantially similarly to the cutting window 114. Specifically, the cutting window 142 is substantially rectangular having dimensions sufficient for locating edges or cutting boundaries thereof, extending substantially parallelly to an axis of elongation of the associated device, outside of the corresponding cutting boundaries of the cutting window 114. In other constructions, the opposite may be true. Thus, as the inner tube 106 and the cylindrical member 130 are rotated with respect to the outer tube 104 and the cylindrical member 122, the opposite cutting boundaries of the cutting windows 114 and 142, respectively, move adjacent and past one another such that any occlusion material present within the windows 114 and 142 will be severed between the cutting boundaries, which may be sharpened, serrated, or include an abrasive of sorts to facilitate thrombus material removal. The cylindrical member 130 has an inner diameter substantially equal to the inner diameter of the inner tube 106 such that occlusion material present therewithin may be aspirated out of the patient's vascular lumen. To further facilitate cutting and aspiration, the dimensions of the cutting windows 114 and 142 are chosen such that, as shown in FIG. 7, the cutting boundaries thereof are diametrically offset on the cylindrical members 114 and 142, respectively. Thus, when the corresponding cutting boundaries, or alternatively, opposing cutting boundaries are aligned, they define a line which extends substantially along a midline of the cylindrical members 122 and 130. The operation of the cutting windows 114 and 142, as well as of the entire thrombectomy device 100, will become more clear herein.

The pigtail member 108 extends a certain, predetermined distance from the distal end 126 of the cylindrical member 122. The pigtail member 108 is formed from a suitable elastomeric material, preferably a low durometer thermoplastic elastomer, such as polyurethane and the like, and is molded into a predetermined substantially twisted configuration for allowing the pigtail member 108 to scour the interior surface of the vascular lumen when rotated, as will be discussed in greater detail later. The pigtail member 108 has an inner diameter portion 144 immediately adjacent the cylindrical member 122 defining an inner diameter substantially equal to the inner diameter of the outer tube 104. Thus, a guidewire lumen 146 is formed in the pigtail member 108 so that a medical guidewire 148 can extend through the axial length of the inner tube 106 and exit through a distal end 150 of the pigtail member 108, as shown in part in FIG. 7.

Because, as noted above, a negative pressure may be applied to the interior of the inner tube 106 to aspirate the intravascular treatment site, the pigtail member 108 includes a reduced or flattened segment 152 located proximally of the distal end 150 of the pigtail member 108. The flattened segment 152 necks down, as shown partially in FIG. 7 and more fully in FIG. 8, such that an inner diameter surface 154 of the pigtail member 108 contracts when the guidewire 148 is removed from the guidewire lumen 146 during operation of the thrombectomy device 100. When the guidewire 148 is inserted into the guidewire lumen 146 such that a distal end of the guidewire 148 extends distally of the distal end 150 of the pigtail member 108, the elastomeric nature of the pigtail member 108 allows the inner diameter surface 154 to expand radially to accept the guidewire 148. When the guidewire 148 is removed from the pigtail member 108, the inner diameter surface 154 contracts sufficiently to substantially seal the guidewire lumen 146 within the flattened segment 152 such that negative pressure applied to the interior of the inner tube 106 will not be allowed to pass distally beyond the flattened segment 152. In this manner, the negative pressure is directed through the cutting windows 114 and 142 against the thrombus, thereby insuring effective aspiration of the intravascular treatment site as well as drawing thrombus material into the cylindrical member 130 for cutting.

In some constructions of the thrombectomy device 100, the flattened segment 152 may be eliminated from the pigtail member 108. However, in order to provide the same effective aspiration of the vascular lumen, a flexible seal member 128 is provided at the distal end 138 of the cylindrical member 130. The seal member 128 may be an elastomeric diaphragm or other suitable construction. The seal member 128 substantially closes the open, proximal end 134 of the cylindrical member 130, and has an aperture 129 therein for allowing passage of a guidewire 148 therethrough. When the guidewire 148 is withdrawn from the aperture 129, the seal member 128 causes the aperture 129 to contract, t,hereby substantially sealing the open end of the cylindrical member 130. This construction also insures effective aspiration through the cutting windows 114 and 142.

When the prime mover causes rotation of the inner tube 106, the pigtail member 108 rotates conjointly therewith. The rotation, combined with the preformed, twisted configuration, of the pigtail member 108 allows the pigtail member 108 to scour an interior surface of a vascular lumen, thereby insuring effective removal of vascular occlusion material. When the pigtail member 108 is torqued in this fashion, it is possible that, because the member 108 is flexible, the pigtail member 108 may buckle under the influence of the applied forces. To substantially prevent this buckling, the pigtail member 108 includes a reinforcing braid 156, formed from a suitable material, such as a metal and the like, which is encased within or overmolded by the elastomer forming the pigtail member 108. If a greater degree of scouring is desired, or if relatively hard deposits are to be encountered, a portion of the braid 156 may be exposed, thereby allowing that portion of the braid 156 itself to scour the vascular lumen interior surface.

Because it is desirable to aspirate the intravascular treatment site to remove vascular occlusion material, it is also desirable to provide a means for irrigation of the treatment site to replace aspirated fluids, or to deliver drug therapies, for example. To do this, an irrigation lumen 158 is provided within the outer tube 104 extending from a proximal end thereof to a position adjacent the proximal end 134 of the cylindrical member 130. The irrigation lumen 158 is defined by an annular region between the inner tube 106 and the outer tube 104. In some embodiments, the distal end of the irrigation lumen 158 communicates with at least one irrigation port 160 included on the pigtail member 108 so that fluids applied to the irrigation lumen 158 can exit through the irrigation port 160 and into the vascular lumen. A plurality of irrigation ports 160 may be provided if desired.

In the particular construction illustrated in FIG. 7, irrigation ports 161 are provided on the outer tube 104 located proximally of a proximal edge of the cutting window 114. Preferably, there are at least two such ports 161 offset diametrically on the outer tube 104 such that irrigation fluid present within the irrigation lumen 161 can flow into the vascular lumen proximally of the cutting windows 114 and 142. In order to prevent irrigation fluid from flowing past the irrigation ports 161 and into the cutting windows 114 and 142, from where it might be aspirated out of the patient's vascular system, thereby preventing it from exiting the removal device 100, a distal portion of the inner tube 106 and/or a proximal portion of the cylindrical member 130 increases in outer diameter. By expanding the outer diameter of the distal portion of the inner tube 106 and/or the proximal portion of the cylindrical member 130, a relatively tight fit is formed between the outer diameter surfaces of the inner tube 106 and the cylindrical member 130 and the inner diameter surface of the outer tube 104. This fit is sufficiently tight to insure direction of irrigation fluid through the irrigation ports 161 and into the vascular lumen, while also providing for rotation of the inner tube 106 with respect to the outer tube 104.

The structure and functionality of the intravascular occlusion material removal or thrombectomy device 100 will become more clear upon reference to the following discussion of a method of using the thrombectomy device 100. Specifically, a medical guidewire 148 is inserted through the inner tube 106, into the guidewire lumen 146, and through the flattened segment 152 in the pigtail member 108. Because of the added rigidity provided by the guidewire 148, the preformed twisted configuration of the pigtail member 108 is substantially straightened, as shown in FIG. 8. Intravascular navigation of the pigtail member 108, and of the thrombectomy device 100 as a whole is facilitated by substantially straightening the pigtail member 108. However, it is to be noted that, due to the elastic memory of the elastomer comprising the pigtail member 108, once the guidewire 148 is removed from the guidewire lumen 146, the pigtail member 108 returns towards its original, twisted configuration for scouring the vascular lumen. Also, removal of the guidewire 148 from the guidewire lumen 146 allows the inner diameter surface 154 of the pigtail member 108 to contract within the flattened segment 152.

The thrombectomy device 100 is navigated intravascularly to the vascular treatment site, and specifically to locate a portion of an occlusion, such as thrombus, adjacent the cutting windows 114 and 142. Once the distal end 102 of the thrombectomy device 100 is properly located adjacent the thrombus, the guidewire 148 can be withdrawn from the pigtail member 108 or, if desired, from the thrombectomy device 100 entirely to leave the lumen defined by the inner tube 106 clear to accept severed thrombus material. As described above, the pigtail member 108 accepts its original configuration and is ready to scour the interior surface of the vascular lumen.

At this point, the prime mover can be activated, thereby energizing the inner tube 106, and causing the inner tube 106 and the cylindrical member 130 to rotate within and with respect to the outer tube 104 and the cylindrical member 122. Simultaneously, a negative pressure can be applied to the interior of the inner tube 106 and the cylindrical member 130. The negative pressure is transmitted to the cutting windows 114 and 142, thereby drawing occlusion material into the openings defined by the windows 114 and 142. Alternatively, or in addition, the distal end 102 of the thrombectomy device 100 may be biased against the occlusion by appropriate means such that occlusion material moves into the opening defined by the windows 114 and 142.

As the inner tube 106 and the cylindrical member 130 rotate with respect to the outer tube 104 and the cylindrical member 122, occlusion material is severed from the occlusion between adjacent, opposite cutting boundaries of the cutting window 114 and the cutting window 142, respectively. Specifically, the inner tube 106 and the cylindrical member 130 rotate such that the cutting windows 114 and 142 are aligned to allow occlusion material to move from outside of the thrombectomy device 100 into the interior of the cylindrical member 130. At this point, the corresponding boundaries of the cutting windows 114 and 142 are adjacent each other and the opposite boundaries are on opposite sides of the cutting windows 114 and 142. As the inner tube 106 and the cylindrical member 130 continue to rotate with respect to the outer tube 104 and the cylindrical member 122, occlusion material within the cylindrical member 130 is compressed between opposite cutting boundaries of the cutting windows 114 and 142, respectively. The compression increases as the inner tube 106 and the cylindrical member 130 progressively rotate until the occlusion material within the cylindrical member 130 is severed between the now-adjacent, opposite cutting boundaries of the cutting windows 114 and 142. If desired, the cutting boundaries of the cutting windows 114 and 142 can be sharpened, serrated, or include an abrasive, as discussed above, for facilitating cutting of the occlusion material.

As the opposite cutting boundaries of the cutting windows 114 and 142, respectively, pass each other as the inner tube 1.06 and the cylindrical member 130 rotate, the cutting window 114 is effectively closed or sealed. As the inner tube 106 and the cylindrical member 130 continue to rotate, the cut occlusion material within the cylindrical member 130 is subjected to the drawing action of the negative pressure applied to the inner tube 106, and is drawn thereby towards the proximal end of the thrombectomy device 100 where the severed occlusion material can be collected in a suitable container. The flattened segment 152 insures that the negative pressure does not extend to the distal end 150 of the pigtail member 108. As the inner tube 106 and the cylindrical member 130 rotate further, thereby bringing the cutting boundaries of the cutting windows 114 and 142 substantially into alignment again, the negative pressure is directed through the cutting windows 114 and 142, thereby drawing more occlusion material to be cut into the cylindrical member 130.

As the inner tube 106 and the cylindrical member 130 rotate, the particular geometries or configurations of the cutting windows 114 and 142 provide for effective thrombus cutting and aspiration. Specifically, because the cutting windows 114 and 142 preferably occupy at most one half of the outer surfaces of the cylindrical members 122 and 130, it is insured that, for at least half of the operating time of the thrombectomy device 100, the intravascular treatment site will be subjected to the negative pressure applied to the inner tube 106. Combining this capability with appropriate rotational speeds of the inner tube 106 and the cylindrical member 130, the operation of the thrombectomy device 100 can be tailored for removal of particular thrombus.

If a given thrombus is relatively dense, well organized or hard, then it may be necessary to utilize a relatively high rotational speed to remove that thrombus from the vasculature. By rotating the inner tube 106 and the cylindrical member 130 at this relatively high speed, the duration of the time periods of cutting window 114 and 142 alignment is relatively short, which means that this thrombus will not be subjected to the negative pressure as long as it might be if the rotational speed of the inner tube 106 and the cylindrical member 130 were reduced. However, this does not compromise effective removal of the thrombi because, as has been determined empirically by experiment, such dense, hard, well organized thrombi are not particularly susceptible to removal by means of aspiration alone, and require a relatively large amount of cutting between the cutting boundaries of the cutting windows 114 and 142. The thrombus and the associated vasculature are subjected to the negative pressure for a duration sufficient to allow for effective removal of thrombus debris from the vascular system.

Alternatively, if the thrombus to be removed is less organized, perhaps comprising a stringy, loose fiber matrix, the rotational speed of the inner tube 106 and the cylindrical member 130 may preferably be relatively slow. Unlike the well organized thrombus, stringy thrombi can be effectively removed by means of aspiration combined with relatively little cutting between the cutting boundaries of the cutting windows 114 and 142. By rotating the inner tube 106 and the cylindrical member 130 at a slower speed, the cutting windows 114 and 142 are aligned for a relatively longer time period, thereby allowing the negative pressure remove a substantial portion of the thrombus by aspiration. As can be appreciated from the foregoing discussion, the inner tube 106 and the cylindrical member 130 can be rotated at a given speed or frequency which can be determined for efficient removal of a given thrombus, rotating at higher frequencies for more organized thrombi, and at lower frequencies for less organized thrombi. By varying the frequency of inner tube 106 and cylindrical member 130 rotation, a treating physician can change the cutting characteristics of the thrombectomy device 100.

The particular configuration of the cutting windows 114 and 142 can also effect the cutting characteristics of the thrombectomy device 100. As noted hereinabove, the thrombectomy device 100 includes cutting windows 114 and 142 having substantially rectangular cutting edge configurations. This rectangular configuration allows the cutting windows 114 and 142 to cut thrombus material between adjacent opposite cutting boundaries or edges, as discussed above. As shown in FIG. 7, these boundaries are substantially linear, extending along an axis of elongation of the cylindrical members 122 and 130. Accordingly, thrombus material can be cut only when opposite, substantially linear boundaries pass each other as the inner tube 106 and the cylindrical member 130 are rotated. Therefore, the cutting windows 114 and 142 define a linear cutting line 162, the location of which is dependent upon the direction of inner shaft 106 and cylindrical member 130 rotation, substantially parallel to the axis of elongation of the cylindrical members 122 and 130, where cutting of thrombus material occurs. Accordingly, it can be seen that the thrombectomy device 100 cuts thrombus material at one, specific location along the circumference of the outer tube 104 defined by the cutting line 162.

Because cutting of thrombus material occurs only at the cutting line 162, thrombus material which has been drawn into the interior of the cylindrical member 130 cannot be cut until it has been moved over to the cutting line 162. Opposition of cutting boundaries occurs only at the cutting line 162, which means that rotation of the inner tube 1.06 and the cylindrical member 130 which carries the thrombus material towards the cutting line 162, effects relatively little cutting. Actual cutting of thrombus material occurs only at a limited location for a short time duration. Also, if a particular portion of a thrombus is appropriately formed, rotation of the inner tube 106 and the cylindrical member 130 may never carry that portion to the cutting line 162, e.g. the portion may recoil like a spring when moved a certain distance by the cylindrical member 130, and never reach the cutting line 162. This can lead to less efficient thrombus removal. Other embodiments of the invention, which can provide more efficient thrombus removal, are discussed hereinbelow.

As the inner tube 106 and the cylindrical member 130 conjointly rotate, the pigtail member 108, which is fixedly attached to the distal end 138 of the cylindrical member 130 is also rotated at substantially the same speed. While the outer diameters of the outer tube 104, the cylindrical member 122 and the pigtail member 108 are chosen such that they are smaller than an inner diameter of the patient's vasculature, thereby facilitating intravascular insertion and navigation of the thrombectomy device 100, the twisted configuration, assumed by the pigtail member 108 upon removal of the guidewire 148 from the guidewire lumen 146, defines an effective outer diameter substantially equal to the inner diameter of the patient's vasculature.

Because the effective outer diameter of the pigtail member 108 is substantially equal to the inner diameter of the patient's vasculature, an outer surface of the pigtail member 108 can scour the interior surface of the particular portion of the vasculature adjacent the pigtail member 108. Specifically, as the pigtail member 108 is rotated intravascularly conjointly with the cylindrical member 130, the outer surface of the pigtail member 108 can contact portions of thrombus or other vascular occlusion, thereby scouring the interior vessel wall of occlusions or otherwise removing portions thereof from the vessel wall. The elastomeric nature of the pigtail member 108 provides the member 108 with sufficient flexibility and elasticity so that rotating contact between the outer surface of the pigtail member 108 and the interior surface of the vessel should not cause substantial injury to the vessel. If a relatively hard deposit is encountered, then that deposit can be contacted by the exposed portion of the braid 156 within the pigtail member 108 to facilitate removal of that deposit. Furthermore, the twisted configuration of the pigtail member 108 can be chosen such that the pigtail member 108 can direct scoured vascular occlusion material removed thereby towards the cutting windows 114 and 142. By directing the scoured material towards the cutting windows 114 and 142, the scoured material can be aspirated through the cutting windows 114 and 142 into the interior of the cylindrical member 130, and from there, aspirated out of the patient, substantially similarly to aspiration of cut thrombus material discussed earlier. In addition, if the pigtail member 108 is utilized with the thrombectomy device 10 illustrated in FIGS. 1 through 3 and discussed earlier, for instance, the pigtail member 108 can provide increased resistance to forces which could shift the device 10 axially within a vascular lumen due to operation of a helical cutter, or similar apparatus, or reciprocation of the cutter intravascularly.

The pigtail member 108 can provide added insurance that thrombus and other occlusions will be removed from the patient's vasculature. This may increase the effectiveness of a particular intravascular treatment, and may reduce the probability of occlusion recursion at the same intravascular site. By combining the effects of the pigtail member 108, the cutting windows 114 and 142, and aspiration through the cutting windows 114 and 142, effective removal of vascular occlusion, such as thrombus and the like, material can be provided by the thrombectomy device 100. While the thrombectomy device 100 may function well, there is always room for improvements which can increase cutting or vascular occlusion material removal and the like.

In an effort to provide more efficient vascular occlusion, such as thrombus and the like, material removal, a number of different cutting window configurations have been developed. Another embodiment of the invention, a thrombectomy device 164, illustrated in FIG. 10, includes cutting windows having a substantially rounded cutting edge configuration. The thrombectomy device 164 is substantially similar to the thrombectomy device 100, hence the like reference numerals for similar structures. The thrombectomy device 164 functions substantially similarly to the thrombectomy device 100, except for the differences to be noted herein. Principally, the major difference between the thrombectomy devices 100 and 164 is that, in the thrombectomy device 164, the cylindrical members 122 and 130 include cutting windows 166 and 168, respectively, which define a substantially circular cutting edge configuration. The circular or radiused configuration of the cutting windows 166 and 168 gives the thrombectomy device 164 cutting characteristics different from the cutting characteristics of the thrombectomy device 100.

The cutting edges of the cutting windows 166 and 168 are substantially radiused, however, it is to be noted that the cutting windows 166 and 168 can be laterally elongated on the cylindrical members 122 and 130 to form a generally oval shape. In order to provide the thrombectomy device 164 with different cutting characteristics, it is only necessary that the edges or cutting boundaries of the cutting windows 166 and 168 be radiused or have a substantially arcuate configuration. In the preferred embodiment of the thrombectomy device 164, the cutting boundaries of the cutting window 166 define a radius larger than a corresponding radius defined by the cutting boundaries of the cutting window 168. The radius defined by the cutting boundaries of the cutting window 166 is substantially equal to an inner radius defined by the cylindrical member 130, thereby positively limiting the size of thrombus material cut and deposited into the interior of the cylindrical member 130 and the inner tube 106. This can insure proper aspiration of the intravascular treatment site.

The thrombectomy device 164, substantially similar to the thrombectomy device 100, cuts thrombus material when opposite cutting boundaries pass each other. Therefore, the cutting windows 166 and 168 of the thrombectomy device 164 cut thrombus material substantially along a cutting arc 170 defined by one of the cutting boundaries or edges of the cutting window 166, depending upon the direction of inner tube 106 and cylindrical member 130 rotation. Of course, these cutting boundaries can also be sharpened, serrated, or coated with an abrasive for facilitating cutting of thrombus.

The thrombectomy device 164 functions substantially similarly to the thrombectomy device 100, except for the differences to be noted herein. When a portion of a thrombus is drawn into the interior of the cylindrical member 130, rotation of the cylindrical member 130 pushes that portion towards the cutting arc 170. However, because the effective location of cutting is now arcuate, and not linear, as it is with the thrombectomy device 100, cutting of thrombus material can occur along the entire arcuate length of the cutting arc 170 because different segments of the cutting boundary of the cutting window 168 pass the cutting arc 170 formed by the opposite cutting boundary of the cutting window 166 depending upon the degree of cylindrical member 130 rotation. Accordingly, cutting of thrombus material can take place over a longer time duration, as compared to the cutting performed by the thrombectomy device 100, as well as at different, multiple locations along the circumference of the outer tube 104, as compared to the thrombectomy device 100 where thrombus cutting occurs at only one location along the circumference of the outer tube 104. Because of this greater amount of cutting performed by the thrombectomy device 164, the thrombectomy device 164 can cut thrombus material more efficiently than the thrombectomy device 100.

Another means for irrigating a vascular lumen is illustrated in FIG. 10. Specifically, a separate irrigation lumen 171 is provided extending through the interior of the inner tube 106. The proximal end of the irrigation lumen 171 is connected to a suitable manifold assembly for supplying irrigation fluid to the irrigation lumen 171. The manifold assembly is constructed such that a guidewire 148 can be disposed through the irrigation lumen 171, thereby allowing the irrigation lumen 171 to provide irrigation fluid and also to deliver a guidewire 148 to the distal end of the thrombectomy device 164. The distal end of the irrigation lumen 171 protrudes through a seal member 169 which extends across the distal end 134 of the cylindrical member 130. The seal member 169 effectively closes the open, distal end 134 of the cylindrical member 130 for aspirating through the cutting windows 114 and 142. When the irrigation lumen 171 is utilized for supplying irrigation fluid to the vascular lumen, the fluid exits the lumen 171 and passes into the vasculature through the irrigation ports 160 in the pigtail member 108.

To provide even greater efficiency in cutting thrombus material, an additional embodiment of the invention, specifically a thrombectomy device 172, illustrated in FIG. 9, has been developed. The thrombectomy device 172 is constructed and functions substantially similarly to the thrombectomy devices 100 and 164, except for the differences noted hereinbelow, hence the like reference numerals for similar structures. The thrombectomy device 172 differs from the devices 100 and 164 in that the thrombectomy device 172 includes cutting windows 174 and 176 on the cylindrical members 122 and 130, respectively, having a substantially V-shaped cutting edge configuration.

Specifically, cutting edges of the cutting windows 174 and 176, respectively, taper towards and terminate at points 178 and 180 such that the cutting windows 174 and 176 define a maximum width, indicated by reference character "W" in FIG. 9, substantially equal to a diameter of the inner tube 106, and a distance, labeled "R" in FIG. 9, substantially equal to a radius of the inner tube 106. This particular configuration of the cutting windows 174 and 176 can positively limit the size of thrombus material that can be deposited into the inner tube 106 after cutting by the cutting windows 174 and 176, thereby insuring proper aspiration of the intravascular treatment site, as discussed hereinabove.

Another construction of irrigation means is also illustrated in FIG. 9. This irrigation means is substantially similar to the irrigation means illustrated in FIG. 7 and discussed hereinabove, except for the differences to be discussed presently, hence the like reference numerals for similar structures. A major distinction of this irrigation means is the addition of an irrigation lumen 173 which operatively connects the irrigation lumen 158 between the outer tube 104 and the inner tube 106 with the irrigation ports 160 in the pigtail member 108. The irrigation lumen 173 extends from a location adjacent the proximal end 134 of the cylindrical member 130 through the seal member 128. Thus, instead of the irrigation fluid being supplied to the vascular lumen at a point proximal of the cutting windows 114 and 142, the irrigation lumen 173 allows the fluid to be supplied through the irrigation ports 160 at a point located distally of the cutting windows 1.14 and 142. Thus, irrigation, drug therapy delivery and the like can be adjusted to meet certain needs.

The thrombectomy device 172 is currently the preferred embodiment of the thrombectomy devices 100, 164 and 172 because of the unique, efficient cutting characteristics provided thereby. The thrombectomy device 172 cuts thrombus material substantially as follows. Upon rotation of the cylindrical member 130 with respect to the cylindrical member 122, thrombus material is caught by a leading cutting edge of the cutting window 176 and is moved towards an adjacent opposite cutting edge of the cutting window 174. Because the cutting edges of the cutting windows 174 and 176 are tapered, cutting of thrombus material can occur along the entire tapered lengths thereof. This provides for efficient cutting, substantially similar to the cutting discussed earlier with respect to the thrombectomy device 164. However, greater cutting efficiency is provided because the cutting edges taper down to points 178 and 180.

Due to the tapered configurations of the cutting edges of the cutting windows 174 and 176, those edges are able to funnel thrombus material towards the points 178 and 180 in response to rotation of the cylindrical member 130. As the thrombus material is funneled, the thrombus is progressively cut until opposite points 178 and 180 on the cutting windows 174 and 176, respectively, pass each other. Thrombus material funneled towards the points 178 and 180 is cut at the points 178 and 180 to completely sever the thrombus portion within the interior of the cylindrical member 130 from the remainder of thrombus within the patient's vasculature. At the points 178 and 180, a relatively smaller amount of thrombus material must be severed, as compared to the amount of material that must be severed by the thrombectomy devices 100 and 164 as the cylindrical member 130 rotates within the cylindrical member 122. In this manner, the thrombectomy device 172 is able to take advantage of the benefits of both cutting along a tapered line and cutting at a point. By combining these benefits, the thrombectomy device 172 is able to cut material more efficiently that the devices 100 or 164. Once the treatment has been completed, the guidewire 148 is inserted into the guidewire lumen 146 in the pigtail member 108, thereby adding sufficient rigidity to the pigtail member 108 to cause it to substantially straighten. Straightening of the pigtail member 108 facilitates intravascular movement of the thrombectomy devices 100, 164 and 172 so that the devices 100, 164 and 172 can be removed from the patient, or positioned adjacent further occlusive material.

Figure 13:
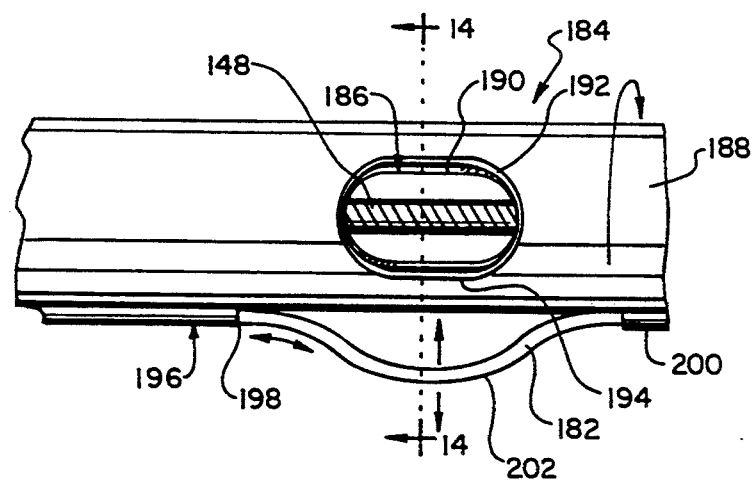
FIG. 13 is an elevational view of another embodiment of the invention including novel means for scouring an interior surface of a vascular lumen to remove unwanted deposits thereon.
Figure 14:
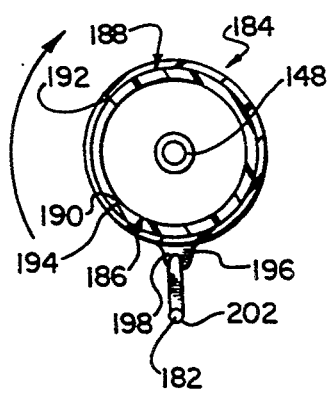
FIG. 14 is a sectional view, taken along line 14—14 of FIG. 13.

The above-discussed embodiments of the invention are shown in the Figures utilizing vascular lumen interior surface scouring means in the form of the pigtail member 108, however, other embodiments of the invention utilize different constructions of the scouring means. An alternative embodiment of the scouring means, specifically an extendable scouring wire 182, is illustrated in FIGS. 13 and 14. Utilization of the scouring wire 182 necessitates certain structural changes in a vascular occlusion material removal or thrombectomy device 184 which make the thrombectomy device 184 different from the thrombectomy devices 10, 100, 164 and 172. Except for the differences noted hereinbelow, the thrombectomy device 184 can be constructed substantially similarly to the thrombectomy devices 10, 100, 164 and 172 discussed earlier.

The thrombectomy device 184 comprises an inner tube 186, shown in section in FIG. 14, coaxially disposed within an outer tube 188 in similar fashion to that discussed earlier. The inner tube 186 has a cutting window 190 and the outer tube 188 has a similar cutting window 192 including a trailing edge 194 disposed thereon such that rotation of the inner tube 186 with respect to the outer tube 188 can cut vascular occlusion material extending through the cutting windows 190 and 192. While the cutting windows 190 and 192 are shown in FIGS. 13 and 14 as having a particular configuration, it is to be noted that the cutting windows 190 and 192 can have any suitable, desired configuration, such as those discussed earlier with respect to the cutting windows 114 and 142, 166 and 168, and 174 and 176.

The construction of the outer tube 188 differs from the previously discussed constructions of the outer tube 104 in that the outer tube 188 includes a scouring wire lumen 196 disposed along an outer diameter surface of the outer tube 188 and extending substantially along the entire axial length of the outer tube 188. The scouring wire lumen 196 is of sufficient dimensions for accepting the scouring wire 182, while not appreciably increasing the profile of the device 184, and for allowing the scouring wire 182 to extend along and beyond the axial length of the thrombectomy device 184 such that a proximal end of the scouring wire 182, not shown, can be appropriately manipulated by a treating physician to scour the interior surface of a vascular lumen. The scouring wire lumen 196 is specifically located along the circumference of the outer tube 188 for locating the scouring wire 182 adjacent the trailing edge 194 of the cutting window 192 on the outer tube 188, the significance of which will become more clear in the following paragraphs. Specifically, the scouring wire lumen 196 is preferably disposed on the outer tube 188 at a location offset substantially ninety degrees in the intended direction of outer tube 188 rotation from a midline of the cutting window 192 parallel to the axis of elongation of the thrombectomy device 184 and the outer tube 188.

In the illustrated construction of the thrombectomy device 184, a distal end 198 of the scouring wire lumen 196 is located proximally of a proximal, latitudinal edge of the cutting window 192. Another lumen or stop member 200 is disposed on the outer surface of the outer tube 188 substantially linearly or coaxially with the scouring wire lumen 196. The stop member 200 has an open proximal end and a closed distal end such that a distal end of the scouring wire 182 can be disposed within the stop member 200, but cannot move distally of the stop member 200. The distal end of the scouring wire 182 may be fixedly attached to the stop member 200 by suitable means, such as an adhesive, solder, braze or the like. In this manner, the scouring wire 182 can extend along the outer surface of the outer tube 188 substantially parallel to an axis of elongation of the thrombectomy device 184. It is to be noted that, while a portion of the scouring wire 182 is disposed within the scouring wire lumen 196 or the stop member 200, another portion of the scouring wire 182, specifically between the distal end 198 of the scouring wire lumen 196 and the proximal end of the stop member 200, is not disposed within a lumen, and is therefore free to bend, bow or flex radially outwardly with respect to the outer tube 188, as is shown in FIGS. 13 and 14, to engage and scour an interior surface of a vascular lumen.

The structure of the thrombectomy device 184 may become more clear upon reference to the following discussion of the operation of the device 184, and specifically, the operation of the scouring wire 182. It is to be noted that the cutting and aspirating operations of the thrombectomy device 184 are substantially similar to the like operations of the thrombectomy devices 10, 100, and 164 discussed hereinabove. Thus, reference should be had to those discussions to refresh the reader's recollection of those operations.

While the inner tube 186 is rotating with respect to the outer tube 188 to cut and aspirate vascular occlusion, such as thrombus and the like, material, the scouring wire 182 can be employed to scour the interior surface of the particular vascular lumen being treated. To do this, a treating physician applies a substantially axially directed force to the proximal, out of body end of the scouring wire 182. This force causes axial movement of the proximal end of the scouring wire 182 towards the distal end of the scouring wire 182 which is fixed in the stop member 200. By moving the proximal end towards the distal end, the effective length of scouring wire 182 disposed within the patient's vascular system is increased. Fixing of the distal end of the scouring wire 182 causes a portion of the scouring wire 182 located between the distal end 198 of the scouring wire lumen 196 and the proximal end of the stop member 200 to expand or bow radially outward away from the outer surface of the outer tube 188. Because the distance between the bowed scouring wire 182 and the outer surface of the outer tube 188 is directly proportional to the length of scouring wire 182 moved into the patient and the scouring wire lumen 196 by the axial force applied by the physician, it is envisioned that a suitable scaling apparatus may be provided at the proximal end of the thrombectomy device 184 for providing the physician with means for positively varying the dimensions of the bow formed by the scouring wire 182, as well as a visual indication of the dimensions of the bow.

Once the scouring wire 182 has been appropriately manipulated to form the illustrated bowed configuration, the scouring wire 182 is ready to scour the interior surface of the vascular lumen. The bowed configuration of the scouring wire 182 is predetermined such that a scouring surface 202 of the wire 182 can engage the interior surface of the vascular lumen being treated. The outer tube 188 is then rotated with respect to the vascular lumen such that the scouring surface 202 passes along the interior surface thereof. To facilitate this rotation, a proximal, out of body end, not shown, of the outer tube 188 is connected to a suitable prime mover, such as a motor, a crank, or the like. When the scouring surface 202 encounters thrombus material along the vascular lumen interior surface, the rotational movement of the scouring wire 182 and the scouring surface 202 should be sufficient to remove at least a portion of that occlusion from the vessel wall. The removed occlusion material can be caught up by aspiration through the cutting windows 190 and 192 as the inner and outer tubes 186 and 188, respectively, rotate so that the material is removed completely from the patient's vasculature. It is to be noted, however, that the rotation of the outer tube 188 does not detract from the vascular occlusion removal actions performed by the cutting actions of the inner tube 186.

Upon completion of the treatment, the treating physician may apply another axial force, directed oppositely to the first-discussed axial force, to the proximal portion of the scouring wire 182, thereby removing a portion of the scouring wire 182 from the scouring wire lumen 196 and the patient's body. This causes the bowed portion of the scouring wire 182 to contract against the outer surface of the outer tube 188, thereby reducing the profile of the distal end of the thrombectomy device 184. By contracting the scouring wire 182, the thrombectomy device 184 is easier to move intravascularly, whether it be to remove the device 184 from the patient, or to position the thrombectomy device 184 adjacent further occlusive material.

Figure 15:
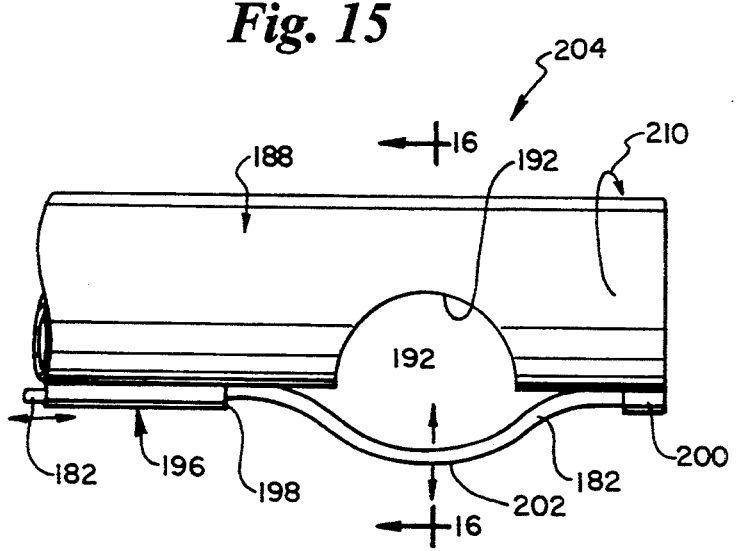
FIG. 15 is a view, similar to that of FIG. 13 of another embodiment of the scouring means.
Figure 16:
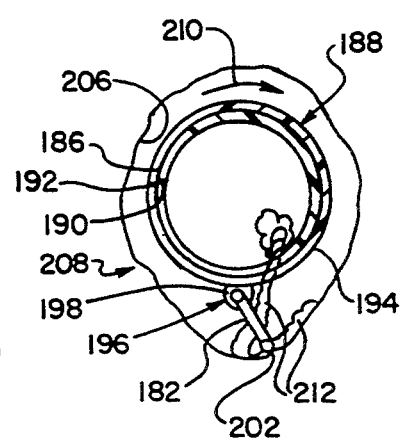
FIG. 16 is a sectional view, taken along line 16—16 of the device of FIG. 15, illustrating the operation of the scouring means within a vascular lumen.

Another embodiment 204, illustrated in FIGS. 15 and 16, of the invention also employs the scouring wire 182, but in a somewhat different manner. Specifically, the embodiment 204 is substantially similar to the thrombectomy device 184, hence the like reference numerals for similar structures, but, as is evident upon comparison of FIGS. 13 and 14 with FIGS. 15 and 16, the location of the scouring wire lumen 196, the stop member 200 and the scouring wire 182 with respect to the cutting windows 190 and 192 has been changed. Instead of the scouring wire 182 being located adjacent the trailing edge 194 of the cutting window 192 substantially ninety degrees offset from a midline, parallel to the axis of elongation of the device, of the cutting windows 190 and 192, the scouring wire 182, in the embodiment 204, is located on the outer surface of the outer tube 188 along the midline, parallel to the axis of elongation of the device, of the cutting windows 190 and 192. Thus, when expanded or bowed as discussed above, the scouring surface 202 lies radially outward from the midline of the cutting windows 190 and 192. This provides the embodiment 204 with an increased ability to remove scoured material from the vascular lumen, as compared to the thrombectomy device 184 discussed earlier.

As shown in FIG. 16, the scouring wire 182 is expanded by the above-discussed method such that the scouring surface 202 of the scouring wire 182 contacts an interior surface 206 of a vascular lumen 208. The outer tube 188 is rotated with respect to the vascular lumen 208 in a direction indicated by arrow 210, which may cause the scouring wire 182 to deflect in a direction opposite to the direction indicated by arrow 210. As the outer tube 188 rotates within and with respect to the vascular lumen 208, the scouring surface 202 of the scouring wire 182 removes vascular occlusion, such as thrombus, material 212 from the interior surface 206 of the vascular lumen 208. Because of the relative orientations of the scouring wire 182 and the cutting windows 190 and 192, combined with the negative pressure applied to the interior of the inner tube 186, as discussed above, for aspirating vascular occlusion material, the material 212 removed by the scouring surface 202 is encouraged to flow through the cutting windows 190 and 192 and into the interior of the inner tube 186, where the material 212 can be aspirated out of the patient. Because the occlusion material 212 is directed towards the cutting windows 190 and 192, in a more direct manner, the embodiment 204 can remove vascular occlusion material separated from an interior surface 206 of the vascular lumen 208 more efficiently than the thrombectomy device 184 of FIGS. 13 and 14.

Figure 17:
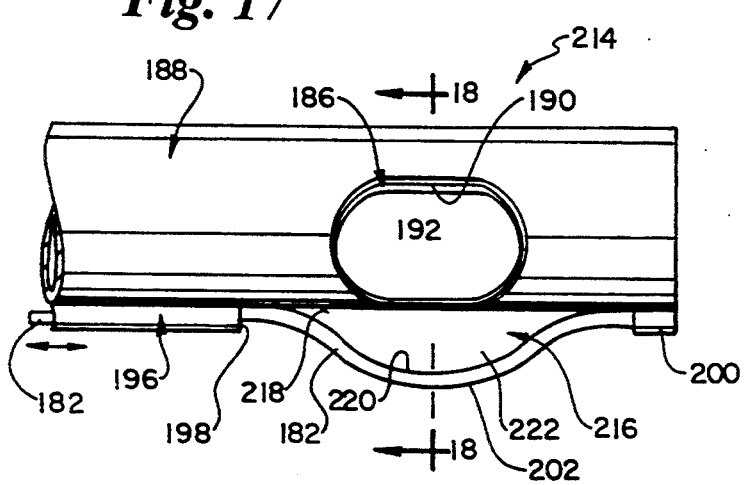
FIG. 17 is a view, similar to that of FIG. 15, of yet a further embodiment of the scouring means including a web member.
Figure 18:
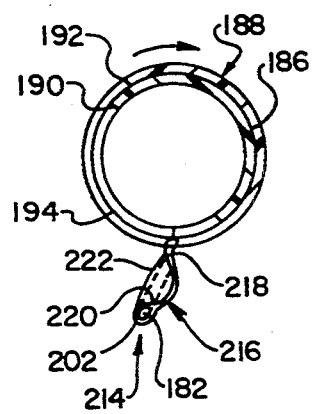
FIG. 18 is a sectional view, taken along line 18—18 of FIG. 17, showing the particular construction of the web.

To further improve removal of scoured material from the patient's vasculature, a vascular occlusion material removal or thrombectomy device 214 is provided, as shown in FIGS. 17 and 18. Like reference numerals are utilized because the illustrated embodiment of the thrombectomy device 214 is substantially similar to the illustrated embodiment of the thrombectomy device 184, however, it is to be noted that the thrombectomy device 214 can also be constructed substantially similarly to the embodiment 204 of the invention, viz. the thrombectomy device 214 may include a scouring wire 182 located adjacent the trailing edge 194 of the cutting window 192, or may include a scouring wire 182 located along the outer surface of the outer tube 188 above and parallel to a midline, which is parallel to the axis of elongation of the device, of the cutting windows 190 and 192.

The thrombectomy device 214 differs from the device 184 and the embodiment 204 in that the device 214 includes a flexible web member 216 for trapping and/or funneling scoured vascular occlusion material into the cutting windows 190 and 192 for removal thereof from the patient's vasculature. The web member 216 may comprise a woven or sheet-like piece of an elastomeric or metallic material having a first side 218 and a second side 220. The first side 218 of the web member 216 is fixedly attached to a portion of the outer surface of the outer tube 188, and the second side 220 of the web member 216 is fixedly attached to a portion of the scouring wire 182 located between the distal end 198 of the scouring wire lumen 196 and the proximal end of the stop member 200 when the scouring wire 182 is in the contracted condition, i.e. lying against the outer surface of the outer tube 188. Thus, when the scouring wire 182 is bowed, as discussed above, it forms a space 222 between the scouring surface 202 of the scouring wire 182 and the outer surface of the outer tube 188. The web member 216 has dimensions sufficient for extending from the outer surface of the outer tube 188 to the scouring surface 202 of the scouring wire 182 when the scouring wire 182 is extended such that the web member 216 covers the space 222. The first side 218 of the web member 216 is therefore substantially linear while the second side 220 is substantially arcuate, thereby allowing the web member 216 to collect occlusion material removed from the interior surface of a vascular lumen by the scouring surface 202 of the scouring wire 182 and to funnel that material towards the cutting windows 190 and 192.

The construction of the device 214, and more specifically, of the web member 216 may become more clear upon reading the following discussion of the operation thereof. Prior to deployment of the scouring wire 182, the web member 216 lies substantially against the outer surface of the outer tube 188 with the first side 218 being adjacent to the second side 220. The scouring wire 182 is deployed or bowed in the same fashion as already described. As the scouring wire 182 is bowed, the scouring surface 202 of the scouring wire 182 draws the second side 220 of the web member 216 away from the outer surface of the outer tube 188 and the first side 218 of the web member 216. The bowed scouring wire 182 forms the space 22 which is covered by the web member 216, thereby causing the web member 216 to assume a substantially convex, arcuate shape which curves or tapers from the second side 220 and the scouring surface 202 towards the first side 218 and the cutting window 192 in the outer tube 188.

As the outer tube 188 is rotated within and with respect to the vascular lumen, the scouring surface 202 scours the vascular lumen interior surface, thereby dislodging occlusion material from the interior surface of the lumen. As the occlusion material is dislodged from the interior surface, the dislodged material is caught by the web member 216. The web member 216, in cooperation with forces generated by rotation of the outer tube 188 and the negative pressure applied to the interior of the inner tube 186, funnels or directs the dislodged occlusion material along the web member 216 towards the cutting window 192 in the outer tube 188. Once the occlusion material has moved sufficiently proximal to the cutting window 192 in the outer tube 188, that material is drawn within the interior of the inner tube 186 by the negative pressure applied therein. Thus, the occlusion material dislodged from the interior surface of the vascular lumen by the scouring surface 202 is removed from the patient's vasculature.

Figure 19:
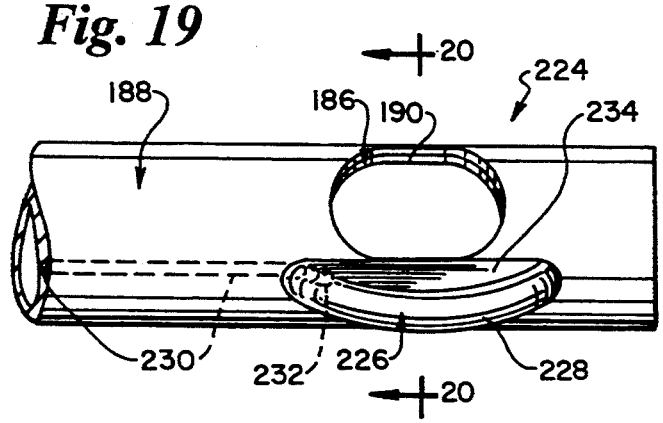
FIG. 19 is a side elevational view of an additional embodiment of the invention including a variable scouring element located adjacent a cutting window.
Figure 20:
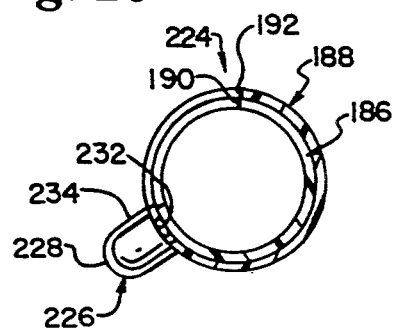
FIG. 20 is a sectional view, taken along line 20—20 of FIG. 19, showing the novel construction of the thrombectomy device.

An additional embodiment of the scouring means is included in a thrombectomy device 224 illustrated in FIGS. 19 and 20. The thrombectomy device 224 is substantially similar to the thrombectomy device 214, except for the differences to be noted herein, hence the like reference numerals for similar structures. Specifically, the thrombectomy device 224 includes scouring means in the form of a dilating member 226 which is located adjacent the trailing edge 194 of the cutting window 192 in the outer tube 188. It is to be fully understood that the dilating member 226 is not intended to bias the thrombectomy device 224 or the cutting windows 190 and 192 against a vascular occlusion to facilitate removal thereof. Instead, a scouring surface 228 formed on the periphery of the dilating member 226 allows the dilating member 226 to effectively scour an interior surface of a vascular lumen, thereby dislodging occlusion material from the vessel wall in substantially the same manner as the scouring wire 182 does. In addition, because the dilating member 226 extends from a linear portion of the outer surface of the outer tube 188, the dilating member 226 can collect occlusion material and funnel that material towards the cutting window 192 in the outer tube 188 for removal from the patient's vasculature, in much the same manner as the web member 216 does.

The dilating member 226, like the scouring wire 182, is movable between an extended position for scouring and a collapsed position for facilitating intravascular movement of the thrombectomy device 224. In the collapsed position, the dilating member 226 lies substantially flatly against the outer surface of the outer tube 188, while, in the extended position, the dilating member 226 expands such that the scouring surface 228 effectively engages the interior surface of the vascular lumen. The dilating member 226 has an axial length larger than the corresponding length of the cutting windows 190 and 192 to insure efficient funneling of material.

An inflation lumen 230 is provided extending through the circumferential thickness of the outer tube 188 from the proximal, out of body end thereof to an inflation port 232 located adjacent the proximal end of the dilating member 226. A proximal end, not shown, of the inflation lumen 230 is connectable with a suitable source of fluid or pressure for inflating and deflating the dilating member 230 as desired. In this manner, fluid applied to the inflation lumen 230 can be transmitted through the inflation port 232 into the interior of the dilating member 226, thereby causing the dilating member 226 to inflate. The dilating member 226 can be inflated to any desired degree, thereby allowing the expanded dimensions of the dilating member 226 to be modified for utilization with a number of differently sized vascular inner diameters.

As the dilating member 226 is inflated, the scouring surface 228 extends radially outwardly away from the outer surface of the outer tube 188 to engage the interior surface of the vascular lumen. As the scouring surface extends, a collecting and funneling portion 234, which functions substantially similarly to the web member 216, is formed by the dilating member 226 extending from the outer surface of the outer tube 188 to the scouring surface 228. Thus, as the outer tube 188 is rotated with respect to the vascular lumen, the scouring surface 228 of the dilating member 226 can dislodge vascular occlusion material from the interior surface of the vessel. The portion 234 can then collect and funnel the dislodged material towards the cutting windows 190 and 192, and, from there, the material can be aspirated out of the patient, as discussed hereinabove with respect to the web member 216.

Figure 11:
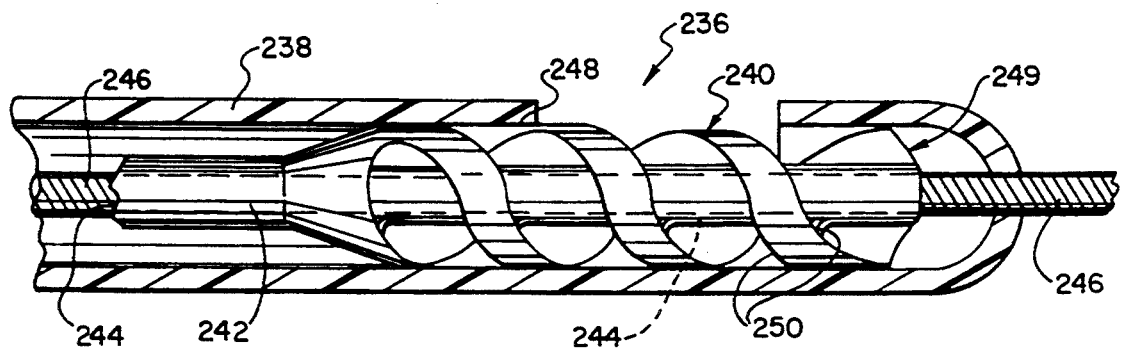
FIG. 11 is a partially sectioned side elevational view of an additional embodiment of the invention comprising a helical cutter.

Another embodiment of the invention, specifically a thrombectomy device 236 is illustrated in FIG. 11 comprising an outer tube 238 and a novel, substantially helical cutter 240. While the illustrated embodiment of the thrombectomy device 236 does not incorporated means for scouring a vascular lumen, it is to be noted that such means could be incorporated without departing from the scope of the present invention. Therefore, it is to be fully appreciated that any of the elements of the various embodiments of the invention discussed herein can be combined with any of the others in any fashion to produce a vascular occlusion material removal device having desired characteristics, i.e. the elements of the various embodiments are interchangeable.

The outer tube 238 is of sufficient dimensions to extend from an out of body prime mover or motor to the desired intravascular treatment site. The outer tube 238 has an inner diameter sufficient to accept a drive shaft 242, a distal portion of which is visible in FIG. 11, which extends from the prime mover to the proximal end of the cutter 240 for transmitting torque from the prime mover to the cutter 240. The drive shaft 242 and the cutter 240 are preferably hollow, thereby defining a guidewire lumen 244 therein for accepting a medical guidewire 246 for guiding the thrombectomy device 236 to the intravascular treatment site. The guidewire lumen 244 may also be used for delivery of ignition fluid. The proximal end of the outer tube 238 is also operatively attached to a source of suction or negative pressure so that occlusion material present within the outer tube 238 can be aspirated out of the patient.

At least one cutting window 248, which may be constructed substantially similar to any of the cutting windows discussed earlier, is disposed on the outer tube 238 adjacent the distal end thereof. A proximal end of the cutter 240 is fixedly attached to the distal end of the drive shaft 242 to facilitate torque transfer thereto, and to locate the cutter 240 adjacent to the cutting window 248 so that vascular occlusion material which enters the cutting window 248 can be cut from the remainder of the vascular occlusion and aspirated out of the patient through the outer tube 238. The edges of the cutting window 248 may be sharpened, serrated, or coated with an abrasive to facilitate vascular occlusion material removal. In addition, the outer tube 238 has a substantially rounded distal end 249 for facilitating intravascular movement of the outer tube 238, and to reduce the probability of trauma to the vasculature.

The cutter 240 has a substantially twisted or helical configuration comprising helical edges 250 which may be sharpened, serrated or coated with an abrasive to facilitate cutting of vascular occlusion material. The edges 250 cooperate with the edges of the cutting window 248 to cut occlusion material therebetween and to deposit the cut material within the interior of the outer tube 238. The direction of rotation of the drive shaft 242 and the cutter 240 may be chosen such that the rotating edges 250 can pull occlusion material radially inward into the interior of the outer tube 238. In addition, the rotating edges 250 may be configured to direct cut vascular occlusion material within the outer tube 238 proximally through the outer tube 238, viz. the edges 250 may cause the cutter 240 to act as an auger for assisting in aspiration of material. Thus, the cooperation of the rotation of the cutter 240 and the edges 250, along with the negative pressure applied to the interior of the outer tube 238 can allow vascular occlusion material cut by the cutter 240 to be aspirated out of the patient.

Figure 12:
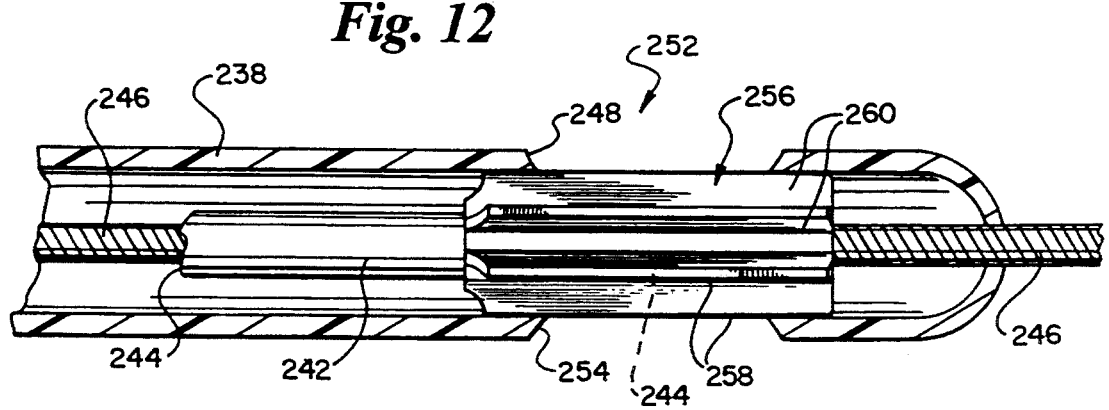
FIG. 12 is a view, similar to that of FIG. 11, of a further novel thrombectomy device having substantially straight cutters.

Yet a further embodiment of the invention, a vascular occlusion removal device 252, is illustrated in FIG. 12. The thrombectomy device 252 is constructed substantially similarly to the vascular occlusion removal device 236 except for the difference noted herein, hence the like reference numerals for similar structures. The illustrated embodiment of the thrombectomy device 252 includes another cutting window 254, but as noted hereinabove, all of the discussed embodiments of the invention may be provided with more than one cutting window.

The thrombectomy device 252 differs from the thrombectomy device 236 in that the device 252 includes a novel cutter 256. Whereas the cutter 240 is substantially helical, the cutter 256 is substantially cylindrical in configuration. The cutter 256 comprises substantially linear edges 258 extending from and substantially axially along an outer surface of the cutter 256, defining spaces 260 between adjacent edges 258. As the cutter 256 rotates within the outlet tube 238, the negative pressure within the outer tube 238 draws the severed material into the spaces 260 between the adjacent cutting edges 258. As the edges 258 pass opposing edges of the cutting windows 248 or 254, the material within the spaces 260 is cut from the remaining vascular occlusion. Because the spaces 260 extend axially along the cutter 256, the negative pressure within the outer tube 238 draws the material within the spaces 260 towards the proximal end of the outer tube 238. When the material within the spaces 260 is severed from the remainder of the vascular occlusion, the negative pressure aspirates the material out of the patient's body.

As is evident from the following discussion, the present invention provides a number of novel intravascular devices for removing vascular occlusion material from a patient. These devices may have particular utility with removing relatively soft vascular occlusion material. By locating a point of cutting adjacent a point of aspiration, efficient removal of vascular material from a patient is provided. In addition, novel methods of removing vascular occlusion material and for treating an occluded vascular lumen are provided.

While preferred embodiments of tile present invention are shown and described, it is envisioned that those skilled in the art may devise various modifications of the present invention without departing from the spirit and scope of the appended claims.

We claim:

1. An intravascular device for use in combination with a movable guide wire to remove vascular occlusion material, especially relatively soft material, such as thrombus and the like, from a vascular lumen within a patient, the device comprising:
   an outer tube having a distal end insertable intravascularly into a patient;
   an inner tube disposed substantially coaxially within the outer tube;
   a cutting window being disposed adjacent the distal end of the outer tube;
   a cutting window being disposed on the inner tube adjacent the cutting window on the outer tube;
   a guide wire fluid seal disposed on the inner tube distal of the cutting window for sealing onto the movable guide wire disposed therein;
   the cutting window on the outer tube being alignable with the cutting window on the inner tube for allowing passage of vascular occlusion material into the inner tube; and
   the cutting window on the inner tube being rotatable with respect to the cutting window on the outer tube for removing vascular occlusion material disposed within the inner tube from a remainder of a vascular occlusion.

2. An intravascular device as defined in claim 1 wherein the cutting window on the outer tube has a cutting edge defining a configuration; wherein the cutting window on the inner tube has a cutting edge defining a configuration; and wherein the configuration of the outer tube cutting edge is substantially similar to the configuration of the inner tube cutting edge.

3. An intravascular device as defined in claim 2 wherein the configuration is substantially arcuate.

4. An intravascular device as defined in claim 2 wherein the inner tube has an inner diameter; and wherein the configuration of either or both the inner tube and outer tube defines a width substantially equal to the inner diameter for positively limiting dimensions of vascular occlusion material passing into the inner tube thereby facilitating aspiration of the vascular occlusion material.

5. An intravascular device as defined in claim 1 further comprising means disposed on the outer tube adjacent the distal end of the outer tube for scouring an interior surface of the vascular lumen.

6. An intravascular device as defined in claim 5 wherein the outer tube has an outer surface; wherein the scouring means comprises a wire disposed along an outer surface of the outer tube; and wherein the wire is flexible for engaging the interior surface of the vascular lumen.

7. An intravascular device as defined in claim 6 wherein the cutting window on the outer tube has a proximal edge and a distal edge; further comprising a wire lumen having a distal end disposed on the outer tube; wherein the distal end of the wire lumen is located proximally of the proximal edge of the cutting window on the outer tube; further comprising a stop member having a proximal end disposed on the outer tube;

wherein the proximal end of the stop member is located distally of the distal edge of the cutting window on the outer tube; and wherein the wire extends through the wire lumen to the stop member such that the vascular occlusion material scoured by the wire will be directed towards the cutting window in the outer tube.

8. An intravascular device as defined in claim 7 wherein the wire has an axial length; wherein the distal end of the wire lumen is offset proximally from the proximal end of the stop member by a distance along the outer tube; wherein the axial length is larger than the distance; and wherein, upon application of a force to the wire, thereby causing the wire to bow between the wire lumen and the stop member.

9. An intravascular device as defined in claim 6 wherein the cutting window on the outer tube includes a trailing edge; and wherein the wire is located adjacent the trailing edge such that vascular occlusion material scoured by the wire may be directed towards the cutting window on the outer tube.

10. An intravascular device as defined in claim 6 wherein the cutting window on the outer tube includes a midline; and wherein the wire is located adjacent the midline such that vascular occlusion material scoured by the wire may be directed towards the cutting window on the outer tube.

11. An intravascular device as defined in claim 1 wherein the outer tube includes a cylindrical member at a distal end thereof; and wherein the cutting window on the outer tube is located on the cylindrical member.

12. An intravascular device as defined in claim 1 wherein the inner tube includes a cylindrical member at a distal end thereof; and wherein the cutting window on the inner tube is on the cylindrical member.

13. An intravascular device as defined in claim 1 further comprising an irrigation lumen within the outer tube for supplying irrigation fluid to the vascular lumen.

14. An intravascular device as defined in claim 13 further comprising an irrigation lumen within the inner tube for supplying irrigation fluid to the vascular lumen; and wherein the irrigation lumen in the inner tube communicates with the irrigation lumen in the outer tube such that irrigation fluid can pass between the irrigation lumen in the outer tube and the irrigation lumen in the inner tube.

15. An intravascular device as defined in claim 1 wherein the inner tube has an open distal end; and further comprising a sealing member extending across the open distal end for allowing passage of a guidewire therethrough while substantially limiting back flow of fluid therethrough.

16. An intravascular device for use in combination with a movable guide wire to remove vascular occlusion material, especially relatively soft material, such as thrombus and the like, from a vascular lumen having an interior surface within a patient, the device comprising:
a rotatable elongate tube having a distal end insertable intravascularly into a patient;
cutting means disposed adjacent the distal end of the elongate tube for cutting vascular occlusion material from a vascular occlusion;
a guide wire fluid seal disposed on the elongate tube distal of the cutting means for sealing onto the movable guide wire disposed therein; and
scouring means attached to the distal end of the elongate tube for scouring vascular occlusion material from the interior surface of the vascular lumen responsive to rotation of the elongate tube.

17. An intravascular device as defined in claim 16 wherein the scouring means comprises a wire located on the elongate tube adjacent the cutting means; and wherein the wire is flexible between an extended position for scouring and a collapsed position where the wire lies substantially along the elongate tube.

18. An intravascular device as defined in claim 17 wherein the cutting means comprises a cutting window having a midline; and wherein the wire is located adjacent the midline such that scoured vascular occlusion material may be directed towards the cutting window.

19. An intravascular device a defined in claim 17 wherein the cutting means comprises a cutting window having a trailing edge; and wherein the wire is located adjacent the trailing edge such that scoured vascular occlusion material is directed towards the cutting window.

20. A method for removing vascular occlusion material, especially relatively soft material, such as thrombus and the like, from a patient's vascular lumen having an interior surface, the method comprising the steps of:
providing an intravascular device including an elongate tube defining a lumen therethrough and insertable intravascularly into a patient, the tube having scouring means for scouring vascular occlusion material from the interior surface of the vascular lumen;
providing a guide wire disposed in the lumen of the device:
inserting the device and guide wire intravascularly into the patient;
positioning the device adjacent vascular occlusion material;
energizing the scouring means to scour vascular occlusion material from the interior surface of the vascular lumen; and
removing vascular occlusion material through the lumen of the device.

21. A method according to claim 20 wherein the scouring means comprises a flexible wire extending along the tube, the wire being flexible between a contracted position where the wire engages the tube and an extended position where the wire engages the interior surface of the vascular lumen, and further comprising the steps of:
flexing the wire into the extended position to facilitate scouring vascular occlusion material from the interior surface of the vascular lumen; and
flexing the wire into the contracted position to facilitate intravascular movement of the wire and the tube.

22. A method according to claim 22 wherein the energizing step comprises:
rotating the tube and the wire such that the wire rotatably engages the interior surface of the vascular lumen to remove vascular occlusion material therefrom.

23. A method according to claim 20 further comprising the step of:
aspirating the vascular lumen to remove vascular occlusion material from the patient.

24. A method according to claim 20 further comprising the step of:
irrigating the vascular lumen.

* * * * *